(12) United States Patent
Corey et al.

(10) Patent No.: US 6,811,990 B1
(45) Date of Patent: Nov. 2, 2004

(54) METHODS AND COMPOSITIONS FOR COUPLED LUMINESCENT ASSAYS

(75) Inventors: Michael J. Corey, 609 165th Ave. NE., Bellevue, WA (US) 98008; Robert J. Kinders, Woodinville, WA (US)

(73) Assignee: Michael J. Corey, Bellevue, WA (US)

( * ) Notice: Subject to any disclaimer, the term of this patent is extended or adjusted under 35 U.S.C. 154(b) by 307 days.

(21) Appl. No.: 10/071,350

(22) Filed: Feb. 8, 2002

Related U.S. Application Data

(60) Provisional application No. 60/269,227, filed on Feb. 13, 2001.

(51) Int. Cl.$^7$ .............................. C12Q 1/66; C12Q 1/32; C12Q 1/34; C12Q 1/02
(52) U.S. Cl. .............................. 435/8; 435/26; 435/18; 435/21; 435/29; 435/968
(58) Field of Search ............................... 435/8, 26, 18, 435/21, 29, 968

(56) References Cited

U.S. PATENT DOCUMENTS 6,653,094 B2 * 11/2003 Anderson et al. ............. 435/26

FOREIGN PATENT DOCUMENTS

| JP | 11-290096 | 10/1999 |
|---|---|---|
| WO | WO 98/28437 A1 | 7/1998 |
| WO | WO 00/75167 A2 | 12/2000 |

OTHER PUBLICATIONS

Corey et al, J. Immunol Methods,vol. 207(1), Aug. 22, 1997, pp. 43–51.*

Bradbury, D.A., et al., "Measurement of the ADP:ATP Ratio in Human Leukaemic Cell Lines Can Be Used as an Indicator of Cell Viability, Necrosis and Apoptosis," *Journal of Immunological Methods* 240:79–92, 2000.

Corey, M.J., et al., "A Very Sensitive Coupled Luminescent Assay for Cytoxicity and Complement–Mediated Lysis," *Journal of Immunological Methods* 207:43–51, 1997.

Crouch, S.P.M., et al., "The Use of ATP Bioluminescence as a Measure of Cell Proliferation and Cytotoxicity," *Journal of Immunological Methods* 160:81–88, 1993.

Kasatori, N., et al., "Cytotoxicity Test Based on Luminescent Assay of Alkaline Phosphatase Released From Target Cells," *Rinsho Byori* 42(10):1050–1054, Oct. 1994, retrieved from *NCBI.gov*, <http://www.ncbi.nlm.nih.gov:80/entrez/query.fcgi?cmd+Retrieve&db=PubMed&list_uids=7996714&dopt=Abstract> [retrieved Aug. 2, 2002].

Mahuren, J.D., et al., Microassay of Phosphate Provides a General Method for Measuring the Activity of Phosphatases Using Physiological, Nonchromogenic Substrates Such as Lysophosphatidic Acid, *Analytical Biochemistry* 298:241–245, 2001.

(List continued on next page.)

*Primary Examiner*—Louise N. Leary
(74) *Attorney, Agent, or Firm*—Christensen O'Connor Johnson Kindness PLLC

(57) ABSTRACT

The present invention provides a set of methods and compositions for homogeneous coupled luminescent assays of cytotoxicity and/or proliferation of cells, as well as for enzymatic activity. In both cases the activities of the enzymes of interest are coupled to production of a high-energy molecule, which serves as a substrate for the production of light by a luciferase, typically in a single reagent mixture, with a useful readout available in 1—5 minutes. Individual cytotoxicity and proliferation signals can be measured from a single sample in 6 minutes or less. The invention also provides a 3-minute, one-step phosphatase assay. The ability to couple the activity of interest to light production in a one-step procedure gives rise to extremely rapid and flexible methods for measurement of cytotoxic effects and enzymatic activities. The assay methods are highly suitable for use in high-throughput screening procedures.

21 Claims, 20 Drawing Sheets

OTHER PUBLICATIONS

Miska, W., and R. Geiger, "A New Type of Ultrasensitive Bioluminogenic Enzyme Substrates," *Biol. Chem. 369*:407–411, May 1988.

Mountfort, D.O., et al., "Evaluation of the Fluorometric Protein Phosphatase Inhibition Assay in the Determination of Okadaic Acid in Mussels," *Toxicon 37*:909–922, 1999.

Olesen, C.E.M., et al., "Novel Methods for Chemiluminescent Detection of Reporter Enzymes," *Methods in Enzymology 326*:175–192, 2000.

Sasamoto, H., et al., "Chemiluminescent Assay of Alkaline Phosphatase Using Phenacyl Phosphate," *Analytica Chimica Acta 306*:161–166, 1995.

Schäfer, H., et al., "A Highly Sensitive Cytotoxicity Assay Based on the Release of Reporter Enzymes, From Stably Transfected Cell Lines," *Journal of Immunological Methods 204*:89–98, 1997.

Ximenes, V.F., et al., "Facile Chemiluminescent Method for Alkaline Phosphatase Determination," *Analytica Chimica Acta 402*:99–104, 1999.

* cited by examiner

Detection of Free Phosphate by PhosTRAK

METHODS AND COMPOSITIONS FOR COUPLED LUMINESCENT ASSAYS

CROSS-REFERENCE TO RELATED APPLICATION

This application is entitled to the benefit of Provisional Patent Application Ser. No. 60/269,227. Feb. 13, 2001.

STATEMENT REGARDING FEDERALLY SPONSORED RESEARCH

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

The present invention is generally directed toward luminescent methods and compositions for measuring various biological events, such as cell death, membrane damage, cell proliferation, or enzyme activities. In these methods, something occurring as a result of enzyme activity is able to produce light, which is detected in a luminometer or other instrument capable of detecting light. The invention is more particularly directed to methods of measuring various biological events, such as cytotoxicity, membrane damage, cell proliferation, enzyme activities, or some combination of these events, by coupling the activities of enzymes, which may be supplied by the investigator, or which may have been released from dead or damaged cells, with production or consumption of high-energy molecules such as adenosine triphosphate (ATP) or nicotinamide adenine dinucleotide (reduced form) (NADH), and subsequently measuring the concentrations of these high-energy molecules by evaluation of the light produced by a light-producing molecule, such as a luciferase.

Cytotoxicity and Proliferation Assays

Assays for cell death and cell proliferation are very widely performed in many areas of biological and clinical research. They may be used to assess the cytotoxic effects of a drug candidate (such toxicity may be either desirable or undesirable), measure the activity of complement, measure programmed cell death (apoptosis), quantify growth-inhibitory or growth-enhancing effects, detect and characterize environmental toxins, determine the sterility or bioburden of a sample, assess drug sensitivity or resistance of a patient's tumor cells or a culture of an infectious organism, or simply determine cell number. One of the most usefull and efficient applications of cell death and proliferation assays is in high-throughput screening (HTS), a collection of methods currently used by many pharmaceutical and biotechnology companies to determine the properties of large libraries of drug candidates very rapidly. However, the methods of determining cell death and proliferation currently in use all suffer from important limitations. Some of these limitations make the assays impractical for use in HTS, and also limit their utility in traditional research environments.

Assays in current use for cell death, or cytotoxicity assays, fall into several categories. One category is "release" assays, in which a substance released by dying cells is measured. Often the substance is an enzyme, such as lactate dehydrogenase (LDH) or glyceraldehyde-3-phosphate dehydrogenase (G3PDH). Traditional enzyme-release assays have exploited the fact that these enzymes create NADH, which can be observed by UV spectroscopy at 340 nm. An alternative is to couple production of NADH to generation of a colored dye, as in the LDH-based CellTiter® assays currently available from Promega. However, these processes are slow and lack sensitivity. For example, the current product from Promega recommends seeding of 5,000–100,000 cell per well, depending on the cell type, and an incubation time with the chromogenic reagents of one hour or more. Other enzymes used in this way include phosphatases, transaminases, and argininosuccinate lyase. These enzymes are typically present in low quantities in most cells, and they do not lend themselves to simple activity assays, making the process of determining cell death cumbersome and insensitive.

Another variety of release assay involves pretreatment of the target cells with a radioactive isotope, generally $^{51}$Cr or $^{3}$H. Upon lysis, the radioactive contents are released and counted in a scintillation counter. Aside from the problems of handling and waste disposal of radioactive materials, these assays also suffer from various artifacts, and are tedious because of the pretreatment and recovery steps required. The same process can also be carried out with fluorescent dyes, such as bis-carboxyethyl-carboxyfluorescein or calcein-AM, but, again, pretreatment is required, and the dyes are spontaneously released at a significant rate by healthy cells.

Another type of release assay is the luminescent assay of ATP released from dead or damaged cells. However, as it is actually used, this is a proliferation assay, and it is discussed further below along with other proliferation assays.

Another category of cytotoxicity assay makes use of dyes which are able to invade dead cells, but not living cells. An example of such a dye is trypan blue. These assays are useful for examining individual cells, but for quantification of overall cytotoxicity they are inefficient because each cell must be counted individually, either by laborious microscopic analysis or by very expensive and time-consuming flow cytometry. Moreover, some modes of death.(such as complement-mediated lysis) are not easily assessed by this method, because the dead cell remains intact for a limited period of time, after which it can no longer be counted because it has disintegrated.

Yet another category of cytotoxicity assays includes those methods directly related to apoptosis. These assays typically look for either protein markers of apoptotic processes or particular effects on DNA that are uniquely associated with apoptosis. The methods are generally slow and tedious, and thus are not suitable for high-throughput screening applications. Another method of studying apoptosis is to look at the ATP:ADP ratios in a cell, which change in a distinct way as the cell enters apoptosis. These assays may be performed by coupled luminescent methods (Bradbury et al. (2000) J. Immunol. Methods 240:79). However, while these methods are useful for qualitative definition of the mode of death, they have no advantages over the ATP-release assay in quantitative determinations of cytotoxicity or proliferation.

Proliferation assays are methods of measuring numbers of live cells. This may be better for some applications than measuring cell death or damage. For example, proliferation assays are able to reveal cytostatic, growth-inhibitory, and growth-enhancing effects which yield no readout in a cytotoxicity assay. Proliferation assays are also in common use as indirect cytotoxicity assays, but there are serious drawbacks with this approach; these are discussed below in connection with the ATP-release assay. Proliferation assays also fall into several categories. Assays of metabolic activity are in widespread use in research laboratories. The commonly used methods make use of tetrazolium salts, which are reduced in living cells to colored formazan dyes. One advantage of these methods is convenience, especially with the newer dyes (MTT and WST-1). The dye is added to the cell culture, and the absorbance of the formazan is read, typically after 0.5–12 hours. However, there are several important disadvantages. Metabolically active cells reduce the dyes at rates much greater than quiescent cells; the readout may therefore be a poor reflection of the cell number. Moreover, the readout is not an instantaneous "snapshot" of the quantity of live cells when the measurement is taken, but rather a complex integral of metabolic activity over the preceding time interval, whose mathematical relationship to the actual live cell number involves the half-life of the dye as well as variations in metabolic activity. Metabolism-based assays are not suitable for measurement of cellular cytotoxicity (for example, the activities of cytotoxic T lymphocytes), or any other assay system in which live cells other than the target cells are present, because these other cells will yield a substantial and often ill-defined background signal. Finally, various artifacts have been associated with the use of these dyes (see for example O'Brien et al. (2000) Eur. J. Biochem. 267:5421–5426; Natarajan et al. (2000) Cancer Detection and Prevention 24:405–414). Although they have not been thoroughly characterized with respect to their effects on cell metabolism, it is known that various agents, such as antioxidants, can interfere with performance of the dyes.

Another kind of proliferation assay actually measures the ability of the cells to grow. This is the colony-forming unit (CFU) assay. It is typically used with cells that grow rapidly and are capable of growth from single cells. The cells are diluted and plated on appropriate growth media, and the colonies are counted when they appear. This method is quite accurate, but is extremely tedious and quite expensive. The labor-intensive aspect of this method is exacerbated by the fact that multiple dilutions of each sample must usually be plated in order to ensure that at least one plate will yield a countable number of colonies.

Finally, cytotoxicity assays can be used as proliferation assays (and vice versa). To use a cytotoxicity assay to count live cells, one simply kills all the cells and performs the assay. (In some cases it may be necessary to wash the cells first, because the readout may depend on a molecule that may have been released into the supernatant by cells that have already died.) The most important example of this approach is the ATP-release assay, mentioned above (Crouch et al. (1993) J Immunol. Methods 160:81). Although strictly speaking this is a cytotoxicity assay, in that ATP released by dead cells is measured, it is rarely used as a direct cytotoxicity assay, because of the very short lifetime of extracellular ATP. Instead, the cells are killed with a lytic agent before the ATP is measured by the luciferase reaction. Thus even though the assay is basically a cytotoxicity assay, if it is to be used to measure cytotoxicity, it is an indirect method, like the other proliferation assays. The ATP-release assay has a number of advantages not enjoyed by many other proliferation assays. It is more sensitive, with a limit of detection of 10–100 cells. It is much faster, with completion of the lysis and assay steps in as little as 3 minutes. Because of the sensitivity, relatively low volumes and small numbers of cells are required. It is really the only assay currently on the market that is sufficiently rapid and sensitive for use in HTS. However, important disadvantages should be noted.

The ATP content of cells is subject to strong metabolic fluctuations, which will cause artifacts. Moreover, the assay can be performed only a single time, immediately after cell lysis; if that opportunity is somehow missed, the experiment must be repeated. Finally, in cytotoxicity mode, the assay suffers from very important drawbacks that are common to all proliferation assays used in this mode. The initial seeding of the wells or reaction vessels with cells must be very accurate, because the cytotoxicity readout depends on differences (which may be small) between numbers of surviving cells, and any scatter in the initial seeding contributes substantially to the noise in the results. This leads to the second problem, which is that a direct readout is almost always preferable to a signal that depends on subtracting two large numbers, as the user must do to use a proliferation assay to measure cytotoxicity. Another very important difficulty is a time-consuming problem with this approach which does not involve the actual assay step. Typically the user adds a potentially toxic compound or agent, waits for death or damage to occur, and then measures the result. The length of time the user must wait depends on the method. If the user is measuring cell death directly, then it can be measured as soon as it occurs, perhaps within minutes. However, if the user is measuring live cells in order to derive the cytotoxicity signal, then the user must wait much longer, until the cytotoxic effect has had sufficient time to cause a detectable difference between the test sample and the control. Furthermore, the required time interval is not known in advance, and if the experiment is stopped too soon, it must be repeated (or abandoned, since the user will not know whether a result showing no difference between test and control is due to the lack of an effect or insufficient time to show an effect). Thus in an HTS mode, where minutes are critical, there is an intervening step in this process requiring an interval of time which may be anywhere from 10 minutes to several days, and which cannot be predicted in advance. This is a serious drawback to the use of any proliferation assay for cytotoxicity work, including the ATP-release assay.

Another type of viability assay, also luminescent, is represented by "CytoLite," a trade name for a mitochondrion-based viability assay (Woods and Clements (2001) Nature Labscene UK March, 2001, 38–39). This method is homogeneous, but requires a 15-minute incubation, and a further 10-minute "dark-adjustment" period before the luminance read; it is therefore too slow for high-efficiency HTS. It is also a viability assay and is subject to all of the drawbacks mentioned above as inherent to viability and proliferation assays.

A cytotoxicity assay based on release of alkaline phosphatase from target cells of killer lymphocytes was described in 1994 (Kasatori et al. (1994) Rinsho Byori 42:1050–1054). This assay method is not suitable for use with other types of cells in general, since most cells do not express alkaline phosphatase in sufficient quantity. Moreover, it involves the use of a substrate whose general effects on cells have not been characterized. It is not a homogeneous or high-throughput assay.

A luminescent cytotoxicity assay described in a 1997 report is based on stable transfection of target cell lines of interest with luciferase or B-galactosidase (Schafer et al. (1997) J. Immunol. Meth. 204:89–98. In terms of sensitivity, this assay represents an advance over conventional release assays; however, the disadvantages of this approach are serious. First, stable transfection itself is a labor-intensive and expensive procedure; yet this must be done for every target cell line of interest if the method of Schafer et al. is to be used. Stable transfection does not always work, and, if it does, may alter the metabolic characteristics of the target cell and thereby severely complicate interpretation of the results of the experiment. The method may not be applicable to cell types outside of these that may be transfected in this manner: expression systems would be different, and the enzymes might be produced in insufficient quantities, in inactive form, or not at all. Moreover, the assay is not homogeneous. Instead the cell culture supernatant must be separated from remaining live cells prior to running the assay. This in itself is a very serious drawback in the high-throughput screening environment, since it adds a complex step to the procedure. Finally, according to the authors, luciferase had a half-life of approximately 30 minutes under the conditions used, and this was found to be inadequate for quantification of cell death in prolonged assays.

Again in 1997, a coupled luminescent method was published (Corey et al. (1997) J. Immunol. Meth. 207:43). This method addressed several of the problems of all of the above methods. This was a release assay, but with important differences from other release assays. G3PDH activity was measured by coupling its cognate glycolytic reaction to the following reaction in glycolysis, which is carried out by phosphoglycerokinase (PGK). The PGK reaction produced ATP, which was then measured by luciferase, which was provided in a separate cocktail, yielding a luminance signal. The limit of detection was <0.1 cell, which was superior to the sensitivity of any other available assay and adequate for almost any application. The assay was relatively fast (~12–15 minutes). Since it provided a direct readout of cytotoxicity, it suffered from none of the disadvantages of proliferation assays used in cytotoxicity mode. The luminance signal continued to increase with time, a feature which allowed the user to decide when an acceptable signal had been achieved "on the fly." Nevertheless, the GPL assay had its own disadvantages which prevented it from being commercially viable. It was cumbersome to execute, in that it involved four transfer steps (cocktail to reaction vessel, sample to reaction vessel, luciferase to luminance vessel, aliquot of reaction to luciferase) and two incubations prior to the actual read. Moreover, because the assay cocktail was not compatible with live cells, tests involving bacteria, erythrocytes, or other non-adherent cells or microbes were still more tedious, because the live cells had to be separated from the supernatant by centrifugation prior to the assay. Finally, like all the methods described above, the assay could be used in cytotoxicity mode or in proliferation mode (the latter by killing all the cells prior to the readout), but not both, with a single sample. These features contributed to the unsuitability of the GPL assay for use in high-throughput screening, especially the necessity of several transfers and the separation of the cells from the supernatant. It was also of limited utility for research use because of its complexity of operation.

As mentioned above, an important disadvantage shared by most cytotoxicity and proliferation assays currently available is that they do not permit measurement of both cytotoxicity and proliferation in a single sample. Release assays, such as the GPL assay, permit quantification of cell rupture or damage, but do not reveal the presence or amount of live cells present. On the other hand, proliferation assays, such as the MTT and ATP-release assays, allow quantification of live cells, in either a non-destructive (MTT) or destructive (ATP-release) mode, but yield no direct information about the degree of cell death that may have occurred. Ideally, the worker would prefer to obtain these two independent pieces of information from the same sample.

In summary, the cytotoxicity and proliferation assays currently available are far from ideal. The traditional release assays suffer from poor sensitivity and speed. Metabolism-based assays are slow, inaccurate with respect to actual cell number, and subject to serious artifacts. CFU assays are too slow and tedious for routine use. ATP-release assays are destructive, one-time assays of moderate sensitivity, and they have numerous important drawbacks as cytotoxicity assays. Although the published coupled luminescent assay (GPL) is superior to the other cytotoxicity and proliferation assays in many ways, it nevertheless is cumbersome and impractical for use in high-throughput screening or research environments because of the processing, numerous transfer steps, and lack of a dual cytotoxicity/proliferation mode.

Phosphatase Assays

Today's drug-discovery environment involves high-throughput screening of inhibitors or other modulators of enzyme activity. Among the enzymes of great interest are phosphatases, which participate in many vital signaling and metabolic pathways. However, assay methods in current use for phosphatases are burdened with a number of drawbacks, including poor throughput or sensitivity, the use of radioactivity, and difficulty of interpretation due to the use of unnatural substrates and/or reaction conditions. Poor throughput and/or sensitivity are often due to the nature of the assay; for example, assays utilizing antibodies against phosphorylated target molecules generally require extended incubations, assays making use of electrophoretic separations are too slow to allow the throughput desired, and assays using radioactivity are inherently incovenient and also suffer from poor throughput. In particular, fluorescence polarization (FP) assays are currently under consideration for high-throughput procedures in some cases. However, these assays, which generally make use of antibodies or other ligands directed against phosphorylated target molecules for detection of phosphatase activity, generally require long incubation times for ligand-target association that significantly reduce the value of these assays in high-throughput screening. These assays also typically involve multiple additions of antibodies or other ligands, and/or wash steps, as well as the design, synthesis, and subsequent ongoing cost of fluorophore-containing biomolecules or synthetic compounds. There is also the possibility that a molecule under study as a modulator of phosphatase activity will give a false signal by binding the fluorophore itself, by otherwise quenching or enhancing its fluorescence, or by blocking the target site on the phosphorylated protein. Finally, many FP assays, and other assays which rely on detection of a phosphorylated target molecule, suffer from an additional disadvantage in that the phosphatase activity yields a negative signal, i.e., a decrease in the phosphorylated molecule which is the target of detection. Such a negative signal is generally considered inferior to a positive signal in enzymology. For one thing, several kinds of artifacts can give rise to a negative signal, including protease contamination or unexpected denaturation of a critical protein. Moreover, a negative signal is usually limited in its dynamic range by its very nature.

Another class of phosphatase assay strategies is based on detection of phosphate liberated by the enzymatic activity. One possibility is radiolabeling of the phosphate group, which can then be separated and counted in some manner. Although this method is still in use in research, it is extremely inconvenient, involving the expense of the label itself, the difficulty and expense of creating or purchasing the labeled compound, a separation step, and the danger and tedium of dealing with the radioactive products. The primary non-radioactive method of detecting phosphate is the use of the malachite green reaction (Mahuren et al. (2001) Anal. Biochem. 298:241), which is quite slow and involves multiple reaction steps, making it unsuitable for high-throughput applications. Another methods of detecting phosphate, which is a coupled luminescent scheme, is useful in devices for environmental or food sampling (Karube, M. (1998) Japanese Patent Application Number 10121688), but involves multiple mixing steps and the use of immobilized enzymes with flow cells in a portable sampling device, making it unsuitable for a high-throughput screening environment. In any case this method has never been shown to be compatible with phosphatase activities. Moreover the oxidizing agents produced in the detection reaction (including hydrogen peroxide) might inactivate a large class of important phosphatases containing active-site thiol groups.

In contrast to the phosphatase assay strategies mentioned above, which can make use of either natural or general peptide/protein substrates, other strategies make use of molecules that are designed more to ease the problem of detection than as ideal substrates for the phosphatase under study. The use of these highly unnatural substrates in high-throughput screening procedures poses a different set of problems, especially problems of interpretation. In most cases the unnatural substrate has quite different kinetic parameters from the actual in vivo substrate. The corollary of this is that when inhibitors or modulators of phosphatase activity are found by such procedures, their characteristics in reactions with the actual in vivo substrate may prove to be very different, especially if competitive inhibition is involved. This is even more likely to be the case if the unnatural substrate has a substantially higher $K_m$ (Michaelis constant) for the enzyme than the natural substrate, since competitive inhibitors identified in such a system may successfully compete for the weakly binding unnatural substrate, but may be ineffective against the strongly binding, natural substrate. Similarly, important inhibitors may not be identified by such a system, especially if the substrate is smaller, more labile than, or kinetically distinct from the natural substrate. For example, p-nitrophenylphosphate is a commercially important substrate for alkaline phosphatase, because it is very labile and yields a colorimetric result, but its use in inhibitor screening applications could lead to false, rejection of good inhibitors. An inhibitor might be strong enough to exhibit useful inhibition of the natural reaction, but not strong enough to prevent most of this very labile ester from being hydrolyzed. Similarly, the inhibitor might block the active site in such a way that the natural reaction is prevented, but small molecules such as p-nitrophenylphosphate, phenacyl phosphate, luciferin phosphate, or 1,2 dioxetanes (see below) can still enter the active site and be hydrolyzed. This could lead to rejection of valuable "hits" in a screening situation. In short, when the reaction being studied is not the same as the natural reaction that is the desired target, there is a substantial risk that the information gathered will not be biologically useful or relevant.

A luminescent phosphatase assay has been reported that employs a 1,2 dioxetane as a substrate (Adam et al. (1996) Analyst 121:1527; Olesen et al. (2000) Methods Enzymol. 326:175). A related method employs a substrate that leads to generation of a dioxetane in situ (Catalani et al. (1999) Analytica Chimica Acta 402:99). A third method employs phenacyl phosphate as the substrate, followed by reaction with lucigenin (Sasamoto et al. (1995) Anal. Chim. Acta 306:161). These methods work only with alkaline phosphatases, and are not readily extensible to other phosphatases, since a new substrate and/or reaction series might have to be designed and synthesized for each phosphatase. In many or most cases this may be impossible or prohibitively expensive. Alkaline phosphatases typically have very different substrate specificities from the protein phosphatases that are of greatest interest in today's biology, such as protein tyrosine phosphatases and serine/threonine phosphatases. Moreover, the methods are not rapid, homogeneous assays; for example, the assay recently reported by Olesen et al. involves 3–4 transfers and at least 2 separate incubations, over a period of at least 30 minutes. This would make it most inconvenient for a high-throughput setting. Another serious drawback of these approaches, discussed above, is the use of unnatural substrates.

Another molecule that has been used as a substrate in phosphatase assays is luciferin phosphate (Mountfort et al. (1999) Toxicon 37:909; Miska and Geiger (1988) Biol. Chem. Hoppe-Seyler 369:407). The principle of the assay is that generation of free luciferin by hydrolysis of luciferin phosphate (catalyzed by the phosphatase) may lead to light production in a reaction that contains luciferase and ATP, but a limiting amount of luciferin. In the 1988 work alkaline phosphate was used, but in the 1999 work, luciferin phosphate was used in an assay of protein phosphatase 2A. In both cited references the assay was slow (30–60 minutes for the enzymatic-reaction step alone), and non-homogeneous (involving at least one transfer after initiation). While it is interesting that protein phosphatase 2A hydrolyzes this highly unnatural substrate, the rate of hydrolysis was so poor that the detection limit was more than 1000-fold worse than by fluorimetric methods (however, these fluorimetric methods also required one hour, involved multiple steps, and required highly unnatural substrates). While it is unknown whether this work can be transferred to other protein phosphatases, it is clear that such hypothetical methods, if possible, would likely be insensitive, very slow, and non-homogeneous, and would also make use of unnatural substrates, with all the disadvantages discussed above.

Accordingly, there is a need in the art for assays that are practical for use in high-throughput screening. The present invention fulfills this need and further provides other related advantages.

SUMMARY OF THE INVENTION

Briefly stated, the present invention provides a variety of coupled luminescent methods and compositions for use in various assays, including for assaying cytotoxicity, membrane damage, cell proliferation, and enzymatic activity. Luminescent methods have an important advantage over other liquid-phase methods in that the sensitivity of luminescent detection of most phenomena is greater than the sensitivity of any other method. For example, electrochemiluminescent (ECL) analysis of Western blots is now the gold standard in sensitivity, and ECL methods are the most sensitive in enzyme immunoassays. "Coupled luminescent" methods are methods in which the activity of the enzyme or enzymes of interest is "coupled" in some manner to production or consumption of a high-energy molecule, such as ATP or NADH, which is a luminescent substrate for one or more of the biological luciferases. Luciferases are enzymes which produce light as they consume such high-energy molecules. Properly designed coupled luminescent assays are able to combine the advantages of specific assays for enzyme function with the very great sensitivity of luminescent detection methods. In these systems the inherent sensitivity of luciferase detection is enhanced by the "amplification" effect of enzyme turnover, which produces thousands, millions, or billions of high-energy molecules for each molecule of enzyme.

In one embodiment of the present invention, the measurement takes place in a one-step "homogeneous" system; a homogeneous system is one in which the sample is mixed with the reagent cocktail, and no separations or further transfers are required prior to readout. The enzyme or enzymes whose activity is being measured (in enzymatic activity mode) or the enzyme or enzymes released from cells (in cytotoxicity, membrane-damage, proliferation, or combined cytotoxicity/proliferation mode) are coupled in a single reaction vessel to production of ATP, NADH, or another high-energy molecule which is a substrate for a luciferase; the luciferase then produces light from the chemical energy of the high-energy molecule. The increase or decrease in the luminance signal is related to the concentration(s) of the enzyme or enzymes whose activity or activities are of interest. Taking cytotoxicity assays as an example, the reagent cocktail may be added to the cells under test before, after, or simultaneously with the potentially cytotoxic agent, depending on the kind of test being performed. If a quantitative determination of killing rate were desired, the cells could be mixed with the agent first and incubated for a fixed interval, after which the reagent cocktail would be added; this would provide an accurate picture of aggregate cell death over time. For maximum speed, reagent cocktail, cells, and the potentially cytotoxic agent could be mixed simultaneously; depending on the speed of killing, a signal could be obtained within minutes, or possibly even less than one minute. Finally, mixing the reagent cocktail with cells before addition of the potentially cytotoxic agent would allow comparison of the viability before and after treatment. These last two modes would also allow the user to follow the whole toxicity reaction in real time. A calibration standard of cells could be used to obtain absolute quantification. Note that the homogeneous nature of this aspect of the invention distinguishes it, in the case of cytotoxicity, from the GPL method, in which the assay reagents are not added in a single reagent mixture; instead the GPL method requires multiple transfers and incubations, first from the sample being tested to the "GP" cocktail; next, following an incubation, from the GP cocktail to the luciferase cocktail, which must also be aliquoted separately. Moreover, the GPL assay is not compatible with live cells, which must be separated by centrifugation, filtration, or another method before the first transfer. In the present invention, all constituents necessary for the assay are added in a single aliquot to the sample being tested, and there is no need to remove live cells from the supernatant.

In a related aspect, the present invention provides a set of methods for measuring cell proliferation. In this mode, the cells are killed by addition of a lytic agent before, after, or simultaneously with addition of the reagent cocktail. If the reagent cocktail is added before the lytic agent, a readout is obtained both of cells killed by processes under study (before addition of the lytic agent) and total cells present (after addition of the lytic agent). If the reagent cocktail is added after the lytic agent, a consistent increase or decrease in the luminance signal may be obtained, representing the total number of cells. If the lytic agent and reagent cocktail are added simultaneously, maximum throughput may be achieved, and the lytic process may be observed in real time (this is also true when the reagent cocktail is added first). Note that this feature also distinguishes the present invention from the GPL method. In the GPL assay, it is necessary to extract live cells from the sample being tested before addition of the GPL reagents, since in many cases these live cells could be killed by the GPL reagents. Thus failure to remove these live cells would lead to a mixed signal of actual cytotoxicity and a portion of the cells that were still alive prior to addition of the GPL reagents. The present invention does not suffer from this limitation, since the reagent mixture is compatible with all types of live cells that have been tested, including several mammalian cell lines, and Gram positive and Gram negative bacteria.

In a preferred embodiment, the present invention provides a set of methods for measuring cell proliferation and cytotoxicity in the same experiment, in a simple, two-step process which maintains the homogeneous nature of the assay. The reagent cocktail is added to cells before, during, or after initiation of the cytotoxic process. Following an incubation to obtain a luminance increase or decrease to obtain a cytotoxicity readout (typically 0.5 to 10 minutes), the lytic agent is added. The luminance increase or decrease following addition of the lytic agent represents the total biomass, alive and dead, at the time of the assay (proliferation readout). The live biomass (as of the time immediately before the lytic step) may generally be calculated by subtracting the toxicity readout from the total-biomass signal. The option of measuring both cytotoxicity and proliferation (or viability) in the same sample distinguishes the present invention from other available liquid-phase cytotoxicity and proliferation assays.

In another aspect, the present invention provides a set of methods and compositions for killing live cells of various types in a manner consistent with accurate reading of luminance due to enzyme release after the lytic step.

In another aspect, the present invention provides a set of methods and compositions for protecting an oxidation- and/or proteolysis-sensitive enzyme released by dying cells from oxidation and/or proteolysis during an initial incubation period, such that enzyme released by cells that die during the incubation period will be measurable at the end of that period.

In another aspect, the present invention provides a set of methods for detecting membrane damage, with or without associated cytotoxicity. Membrane damage associated with cell death is detected as cytotoxicity as discussed above. Membrane damage can also be detected separately from cell death (i.e., non-fatal damage) by performing assays by one of the specified methods for enzyme release, followed by an optional recovery phase and subsequently by a proliferation or viability assay, such as the CFU assay, a metabolism-based assay, or the proliferation mode of the present invention.

In another aspect, the present invention provides a set of methods of detecting enzymatic activity by coupling the enzymatic activity to production or consumption of a high-energy molecule that is a luciferase substrate.

In another aspect, the present invention provides a set of methods for optimizing a coupled luminescent assay for (1) time linearity, (2) linearity with enzyme or cell number to be measured, (3) compatibility with cells of various types, (4) homogeneous use, and (5) use in high-throughput screening (HTS).

In another aspect, the present invention provides a set of methods for optimizing the storage conditions of reaction cocktails and reaction cocktail ingredients with respect to physical form, storage of mixed or separate ingredients, temperature of storage, and time of storage.

In another aspect, the present invention provides a set of methods for automatic reduction of complex data by linear regression. These methods compute linear fits for all possible time ranges within a given data set and (1) report slopes and/or correlations for all ranges, and/or (2) select the time range or ranges with the highest correlation(s) and report these ranges, correlations, and slopes, and/or (3) select a time range or ranges with certain given fit characteristics from a given sample or set of samples (which could be calibration or other standards) and apply that range or those ranges to all or a subset of the remaining samples, and/or (4) detect and report exceptional aspects of data obtained from a given sample or samples, or from the entire run, such as poor signal strength, linearity, time correlation, or correlation with expected values, and/or (5) evaluate the characteristics of the run, such as linearity and/or signal strength, and either make an automated decision to stop or continue reading the samples or report the run characteristics to the user to allow the user to make that decision.

In another aspect, the present invention provides a set of methods of measuring cytotoxicity, membrane damage, cell proliferation, and enzymatic activity with the use of a stop reagent. The increase or decrease in the luminance signal is wholly or partially stopped by the reagent, allowing the user to treat the ending luminance value as the readout of the assay, such endpoint reading to take place at any time convenient to the user In another aspect, the present invention provides a set of methods for HTS of compounds for any of a number of desirable or undesirable characteristics: (1) desirable cytotoxicity against an identified target, which may be a cancer cell type or an infectious microorganism; (2) undesirable cytotoxicity against normal cell types in a drug candidate; (3) growth-affecting characteristics; (4) membrane damage; or (5) inhibitory or rate-enhancing properties in a given enzymatic system. These methods involve preformulation of the reaction cocktail and preloading this cocktail into an injector of a luminometer, followed by homogeneous or non-homogeneous assay of the rate of increase or decrease in the luminance signal and either automated data reduction, non-automated data reduction, or the use of a stop reagent and a single readout. The HTS run may be (1) terminated after a single or fixed number of reads, (2) terminated automatically when certain criteria are achieved, or (3) terminated at the user's discretion.

In another aspect, the present invention provides a set of methods for testing an individual patient's cancer tumor cells or infecting microorganisms for sensitivity or resistance to a potential drug, drug mixture, or panel of drugs or drug mixtures.

In another aspect, the present invention provides a set of methods for detecting and quantifying apoptosis (programmed cell death). This may be accomplished as under the description of cytotoxicity measurement, above, or by coupled luminescent detection of the increase levels of nuclear G3PDH associated with apoptosis, or by a combination of these methods.

In another aspect, the present invention provides a set of methods for detecting the presence of live cells in environments that are intended to be sterile or have low bioburdens. This would be accomplished by taking a sample (either a liquid sample or a swabbed sample, which can then be transferred or washed into a liquid sample), using a lytic agent, and performing a coupled luminescent assay as described elsewhere under proliferation assays.

In another aspect, the present invention provides a set of methods for very sensitive detection of environmental toxins. This would be accomplished by mixing an environmental sample, such as an aliquot of seawater or residue from a wash of shellfish or other food samples, with a coupled luminescent reaction cocktail in the presence of a cell type known to be sensitive to the toxin in question, and measuring the resulting cytotoxicity.

In another aspect, the present invention provides a set of methods of detecting and/or quantifying free phosphate by coupling the presence of free phosphate to production of ATP via the activity of G3PDH and PGK, which are both supplied in the reagent mixture. Detection and/or quantification of free phosphate is of importance in biochemistry, enzymology, environmental science, and other areas.

In a second preferred embodiment, the present invention provides a set of methods for detecting the enzymatic activity of a phosphatase by quantifying the phosphate produced by the reaction of the phosphatase, which is accomplished by coupling the presence of free phosphate to production of ATP via the activity of G3PDH and PGK, which are both supplied in the reagent mixture. In this embodiment, the present invention enjoys a number of advantages over other phosphatase assays in current use, including great speed, extreme simplicity of operation, and the ability to use natural substrates, or, when they are unavailable, appropriately chosen phosphorylated peptide or protein substrates, or other phosphorylated molecules as similar as is practicable to the in vivo substrates.

In another aspect, the present invention provides a set of methods for detecting activity of intracellular phosphatases by optionally measuring phosphatase activity by the method described above before lysis, lysing the cells by one of the methods provided in the invention or by another method, and again measuring phosphatase activity. The principle may also be applied to measurement of phosphatase activity inside particular cellular organelles.

In another aspect, the present invention provides a set of methods for measuring activity of specific phosphatases, for which specific substrates are available, against a background of other phosphatases and/or free phosphate by measuring the quantity of phosphate present or the rate of phosphate production by the methods provided, adding the specific substrate or substrates, and again measuring the quantity of phosphate present (after a time interval of the user's choice) or the rate of phosphate production.

These and other aspects of the present invention will become evident upon reference to the following detailed description and attached drawings.

DETAILED DESCRIPTION OF THE INVENTION

Figure 1:
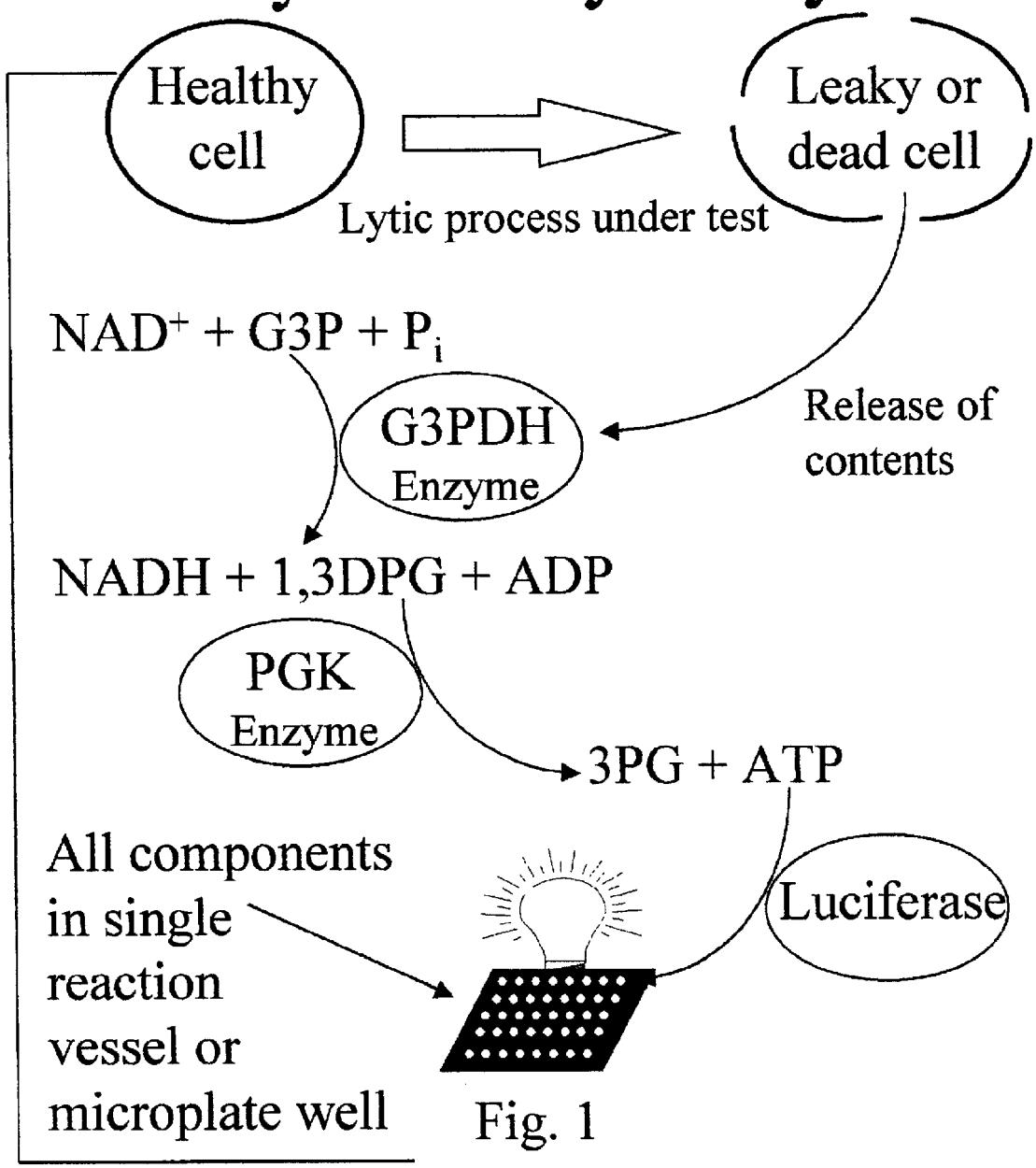
FIG. 1 is a schematic diagram of a preferred mode of the present invention known as "DeathTRAK". An important advantage of DeathTRAK is that all of the depicted events and reactions can take place in a single reaction vessel, and that a direct readout of the signal is obtained with no further sample processing (i.e., it is "homogeneous"). Abbreviations used in FIG. 1: NAD+: nicotinamide adenine dinucleotide (oxidized form); G3P: glyceraldehyde-3-phosphate; $P_i$: phosphate ion; G3PDH: glyceraldehyde-3-phosphate dehydrogenase; NADH: nicotinamide adenine dinucleotide (reduced form); 1,3DPG: 1,3 diphosphoglycerate; ADP: adenosine diphosphate; PGK: phosphoglycerokinase; 3PG: 3-phosphoglycerate; ATP: adenosine triphosphate.

In one aspect, the present invention is directed toward methods of measuring cytotoxicity. In a preferred embodiment, cytotoxicity is measured in a homogeneous assay in a microplate luminometer. The luminance signal is produced by firefly luciferase acting on adenosine triphosphate (ATP), which in turn is produced by the coupled reactions of glyceraldehyde-3-phosphate dehydrogenase (G3PDH) and phosphoglycerokinase (PGK), two consecutive enzymes of the glycolytic pathway. G3PDH, a very abundant enzyme in all known cells, is measured to quantify release (and therefore cell death and/or membrane damage), while PGK, which is generally not so abundant in cells, is supplied in the reaction cocktail, along with glyceraldehyde-3-phosphate (G3P), nicotinamide adenine dinucleotide oxidized form (NAD+), inorganic phosphate (Pi), dithiothreitol (DTT), adenosine diphosphate (ADP), the components of the luciferase reaction, and appropriate buffers and salts (see FIG. 1 for a schematic diagram of the assay, and Example 1 for additional details of the components). Essential to the invention is the fact that G3PDH is abundant in all living cells; therefore the user can be confident that the invention will be useful in measuring cytotoxicity and/or proliferation of a specific cell type without prior testing. Moreover, G3PDH is a natural component of the cells, and does not need to be introduced into the cells in any manner. This distinguishes the present invention from all methods which require prelabeling of the cells, or transfection, transformation, or other methods of introducing proteins or other molecules into the target cells in order to generate a signal in a later step.

It should be noted that as with any assay method, the methods of the present invention are subject to incorrect results if certain substances which interfere with the assay components are present. As an example, if a user is employing one of the modes herein described for screening a compound library for cytotoxic effects, and one of the compounds in the library happens by chance to be an inhibitor of one of the enzymes essential to operation of the mode in use, an incorrect signal may be obtained. As in all screening studies, it is desirable to follow up screening runs with further experiments using independent methods. However, the range of substances of interest that interfere with DeathTRAK is likely to be far smaller than with the MTT and other metabolic assays, as pointed out above. Likewise, the ATP-release assay is vulnerable to compounds that interfere with luciferase activity, as well as the whole set of agents that affect the ATP charge of living cells.

Example 1 shows an assay of the effects of a cytotoxic agent on cells derived from human prostate cancer. In this case the cytotoxic agent is the alternative pathway of complement, but it may be a candidate drug molecule, food additive, environmental sample, or any other substance or mixture in liquid form with the potential to cause cytotoxicity or membrane damage. The experiment was performed to test the effects of a monoclonal antibody directed against complement Factor I (FI) on complement-mediated lysis of the PC-3 cell line.

A preferred mode of the invention involves the simultaneous reaction of three enzymes, while maintaining compatibility with live cells, protecting the G3PDH enzyme from inactivation or denaturation, and allowing individual measurements of both cytotoxicity and proliferation in the same sample. The process of meeting the requirements of the enzymes and cells is described in Example 2, while the combined cytotoxicity/proliferation mode is described in Example 8, below. Under Example 2, the process of finding a buffer that yielded high signal strength and was compatible with live cells was carried out; concentrations of PGK and ADP were optimized; and a comparison of time-linear fits with single-point readouts shows that single data points may be used effectively to report DeathTRAK results, after as little as 2.6 minutes. It is necessary to adjust the concentrations of various reagents in order to obtain satisfactory performance while meeting the various constraints imposed by the system. Examples of such constraints are: (1) the assay cocktail must be homogeneous; i.e., after the cocktail is loaded into the injector, the only mixing step should be the automated injection of cocktail into sample, with no separations needed; (2) the cocktail must not significantly damage live cells in the time-frame of the assay; (3) the cocktail must contain necessary reagents in concentrations adequate to support strong signals and/or extended reactions, without yielding excessive background signals; (4) the time-dependent response of the assay must be as near linear as possible, over as wide a dynamic range as possible; and (5) storage characteristics of the assay cocktail must be satisfactory for widespread use. Examples of constraints encountered within category (3) include: (A) the phosphate ion is necessary for G3PDH activity and must be present at adequate levels, but it is a potential inhibitor of enzymes which metabolize ADP/ATP, and its level must therefore be kept in check; (B) the PGK enzyme is essential for production of ATP, and in many cases it is a limiting reagent (see Example 2B); however preparations of PGK are almost always contaminated with small amounts of G3PDH, which adds to the dynamic background signal during the reaction, and also tends to convert G3P to 1,3 DPG during storage, contributing to static background, and (C) ADP is an essential component and is often limiting (see Example 2C), but ADP preparations are often contaminated with ATP, which contributes directly to the static background.

Example 2A shows the process of developing a cocktail which is compatible with live mammalian cells and shows an adequate response to the test enzyme G3PDH. The IMDM growth medium and phosphate-buffered saline (PBS) are both nearly isotonic with respect to mammalian cells and were chosen for a titration assay to determine the point at which the assay response would be optimal. Since phosphate ion is a potentially exhaustible component, concentrations with greater phosphate concentrations were preferred in cases of similar performance.

Figure 2:
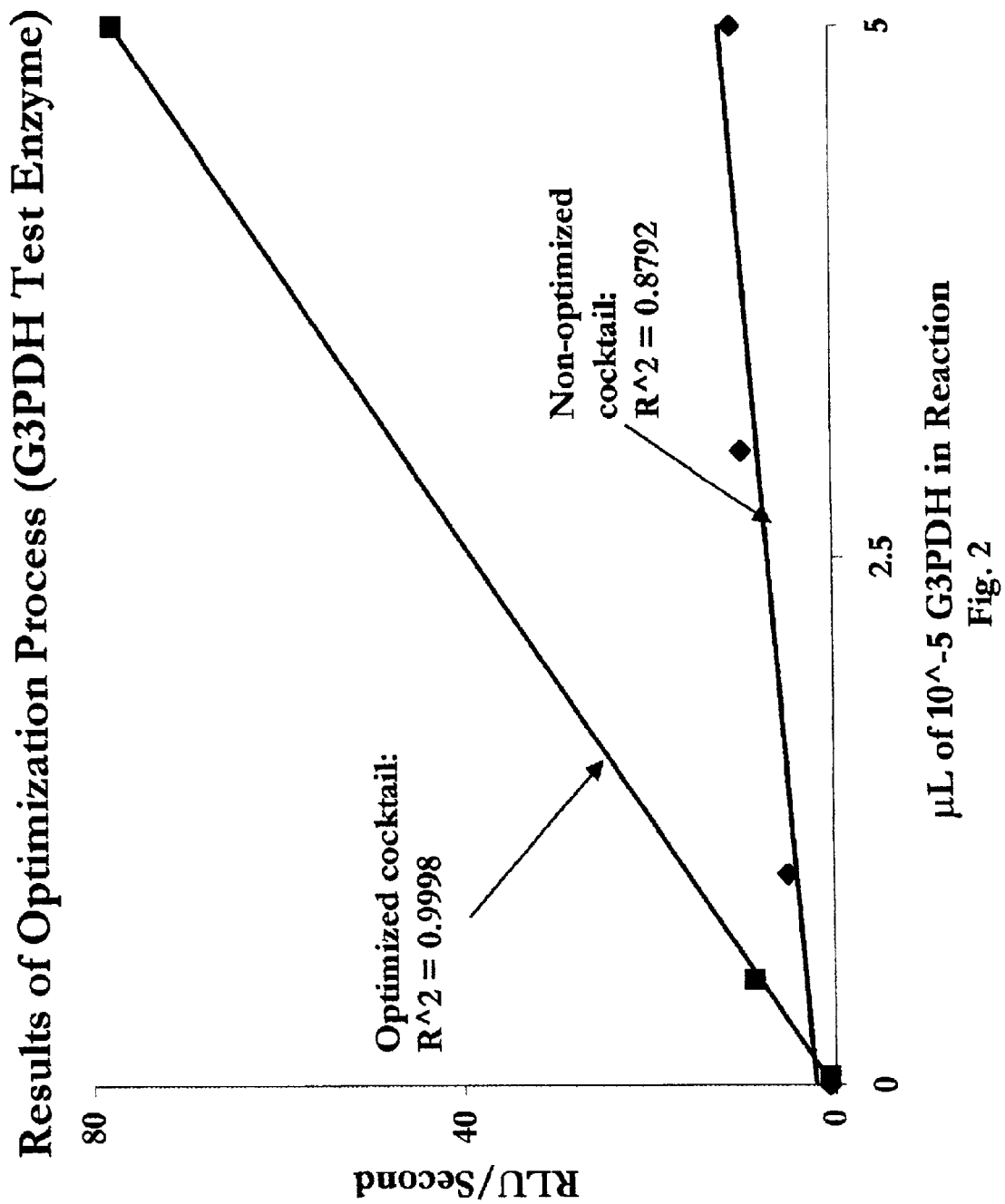
FIG. 2 shows the results of optimizing the DeathTRAK homogeneous cocktail, using the G3PDH test enzyme. Results with the unoptimized and optimized cocktails are shown (along with $R^2$ correlation values), using similar ranges of enzyme concentrations. Error bars are displayed but are too small to see.

After the optimization process of Example 2A the reaction cocktail was compatible with live cells, but exhibited only modest linearity and sensitivity with the test enzyme. FIG. 2 shows a comparison of the linearity and sensitivity before and after optimization steps represented by Examples 2B and 2C. Errors (standard deviations) are shown in this graph but are too small to be visible. The $R^2$ was improved by optimization from 0.8792 to 0.9998, while the luminance response per unit enzyme was enhanced by over 7-fold. The assay of the optimized cocktail was performed with ten-fold serial dilutions. The significance of this plot is not merely the fact that the linear correlation is vastly improved, but also the fact that the line passes precisely through the origin, indicating an excellent proportionality between the amount of enzyme added and the signal response. Example 2B shows the first of these optimization processes. As explained above, PGK is an important component of DeathTRAK, but if it is present in excess, then contaminating G3PDH adds to both static and dynamic background signals. PGK was therefore titrated over two orders of magnitude to determine how much greater a concentration could be present without unacceptable effects on the background and assay linearity.

The results of PGK optimization dramatically improved the response of DeathTRAK, but the improved signal exacerbates the saturation problem that is seen in the unoptimized cocktail even at moderate signal strength. Example 2C shows that an increased starting concentration of ADP led to an enhanced signal.

Figure 3:
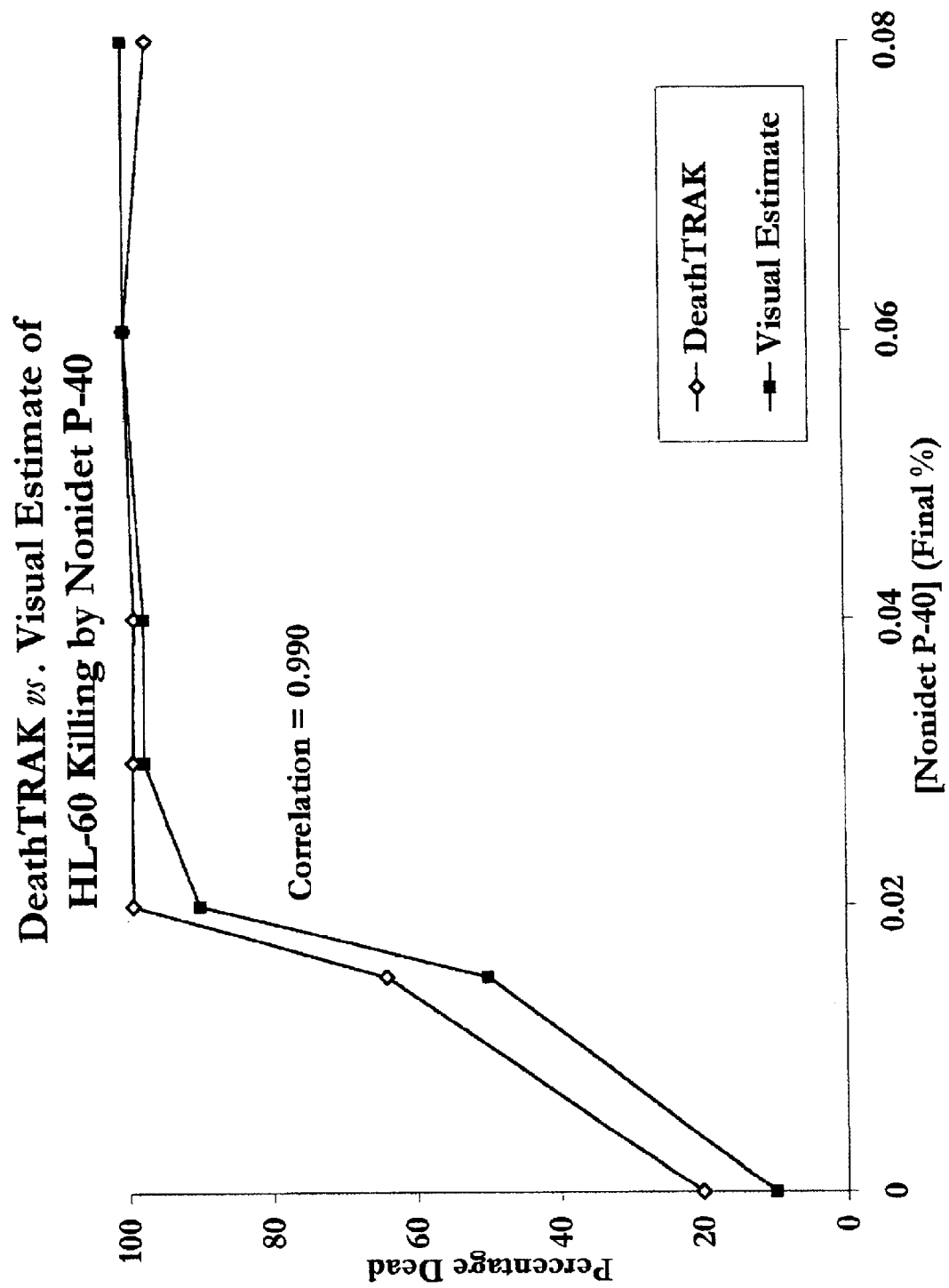
FIG. 3 shows the results of cytotoxicity measurements of HL-60, compared with visual estimates of cell death.
Figure 4:
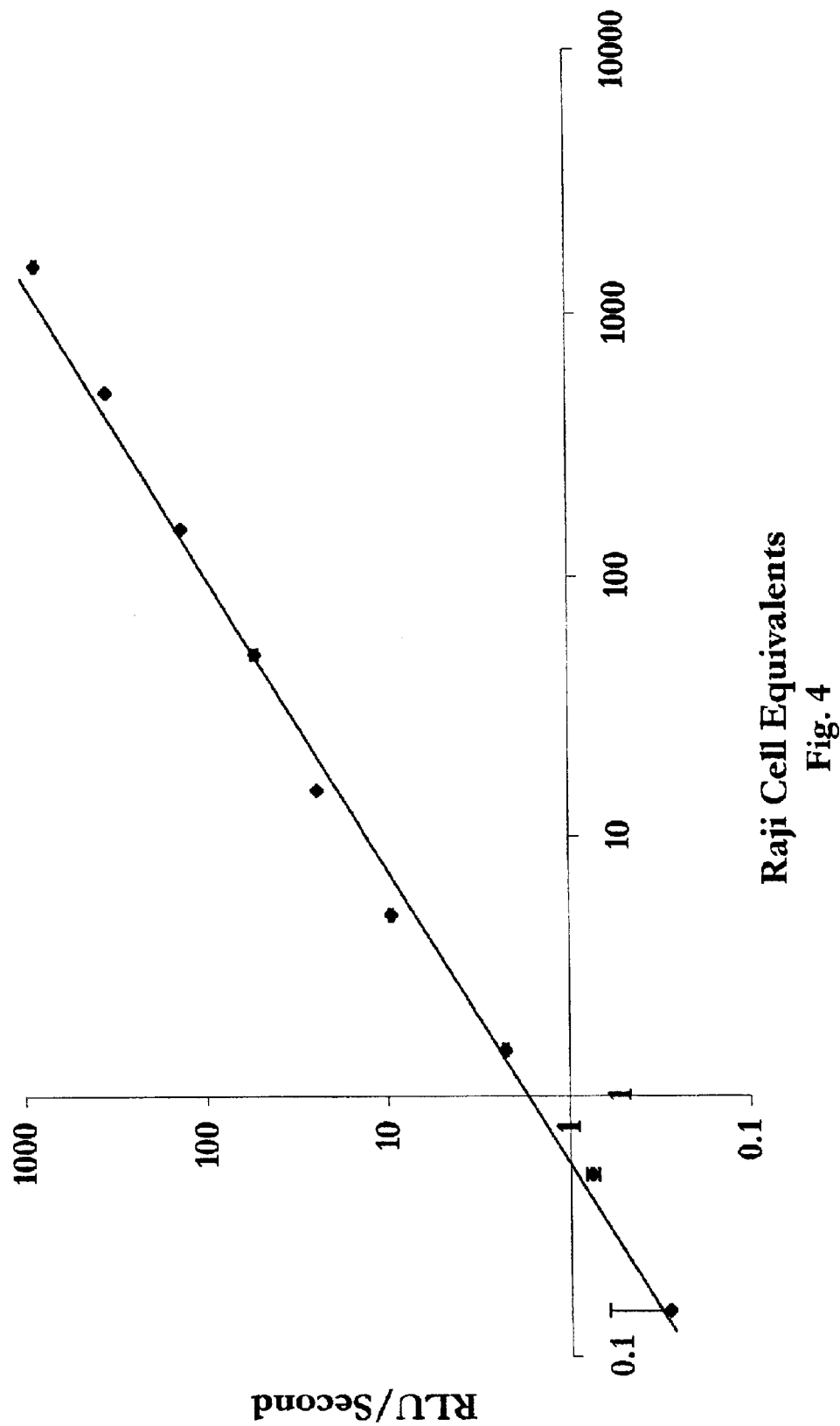
FIG. 4 shows the dynamic range of the optimized Death-TRAK assay with lysed Raji cells. The response is nearly linear over four orders of magnitude. The graph is a log-log plot. Error bars are displayed but are too small to see, except for one side of the error bar at the lowest point (the other side of the error bar enters negative values and cannot be displayed on a log-log plot).

Example 2D shows the results of various tests of the optimized cocktail. FIG. 3 shows the results of an experiment in which the DeathTRAK results are compared with another method (visual inspection) of determining cytotoxicity, yielding a correlation coefficient between the two methods of 0.990. This high degree of correlation between the results of measuring cytotoxicity by the methods of the present invention and the very distinct method of direct visualization adds to the confidence level and value attached to the invention. FIG. 4 shows the data obtained from Raji cells that were intentionally lysed prior to the assay, demonstrating a good response over four orders of magnitude. A highly reproducible signal was also obtained with the G3PDH test enzyme.

In another aspect, the present invention provides methods and compositions for optimizing stability during storage of a reaction cocktail for use in a coupled luminescent assay. Example 2E shows the effects of lyophilization vs. freezing of the components in various combinations. This shows that freezing is a superior means of storage. Example 2F is a test of the effect of frozen storage vs. storage at 4° C., including especially influence on the static background signal. Again, freezing proved to be a much better method of storage.

Example 2G shows the lag phase that was experienced when the homogeneous assay was first used and provides methods for overcoming this problem.

In another aspect, the present invention provides methods and compositions for a single-timepoint coupled luminescent assay, making use of a stop reagent to end the production of the high-energy molecule that is the luciferase substrate, while allowing the luciferase reaction to continue. In a preferred embodiment of this concept, an inhibitor of G3PDH or PGK is used to stop production of ATP in the DeathTRAK reactions of Examples 1 and 2. This results in a fairly constant luminance signal and permits the user to read a single number at the end of a fixed interval, rather than having to deal with data reduction of a time-dependent signal. It is also possible to perform a single read without a stop reagent, but the stop reagent allows the read to be done at a time convenient to the user, multiple times, or for an extended period. Example 2H demonstrates the use of a stop reagent with the DeathTRAK assay. Other candidate stop reagents are the synthetic peptide MEELQDDYEDMMEEN-NH2, which was derived from the N-terminus of human erythrocyte anion transporter, band 3 (Eisenmesser E Z and Post C B, *Biochemistry* 1998 January 20;37(3):867–77); vanadate ion (Crans D C, Simone C M, *Biochemistry* 1991 July 9;30(27):6734–41); iodoacetic acid (Baker M S, Bolis S, Lowther D A, *Agents Actions* 1991 March;32(34)299–304; Rego A C, Areias E M, Santos M S, Oliveira C R, *Neurochem Res* 1999 March;24 (3).351–8); pentalenolactone (Ikeda M, Fukuda A, Takagi M, Morita M, Shimada Y, *Eur J Pharmacol* 2001 May;411 (1–2):45–53); acrylamide (Anuradha B, Varalakshmi P, *J Appl Toxicol* 1999 November–December;19(6).405–9); 3-chloro-1-hydroxypropanone (Jones A R, *Reprod Fertil Dev* 1997;9(6):577–8 1); koningic acid (Nakazawa M, Uehara T, Nomura Y, *J Neurochem* 1997 June;68(6): 2493–9); (S)-3-chlorolactaldehyde (Jones A R, Porter L M, *Reprod Fertil Dev* 1995;7(5):1089–94); 3-bromo-1-hydroxypropanone (Porter L M, Jones A R, *Reprod Fertil Dev* 1995,7(1):107–1 1); various phosphorylated epoxides and alpha-enones (Willson M, Lauth N, Perie J, Callens M, Opperdoes F R, *Biochemistry* 1994 January 11;33(1): 214–20); various phosphonates (Li Y K, Byers L D, *Biochim Biophys Acta* 1993 June 24;1164(1):17–21; however these compounds might also inhibit luciferase); or other compounds in the literature, some of which were developed as potential therapeutic agents for trypanosomiasis. Any molecule which inhibits G3PDH and/or PGK, but inhibits luciferase to a lesser or insignificant degree, might be used.

In another aspect, the present invention provides automated methods for analyzing data obtained from coupled luminescent reactions. Since these reactions are due to continuous enzyme activity, the luminance signal continues to increase with time during the reaction, unless a stop reagent is used. Thus there are several methods of reducing the luminance data to a single value, which may represent either a rate (change in luminance per second, commonly reported as Relative Luminance Units or RLU/second) or an absolute luminance level, read after a precise length of time, and/or with the use of a stop reagent. The case in which the readout is a single, absolute luminance level requires little additional analysis (although some aspects of the present invention could be used as a quality-assurance procedure even in these cases). The calculation of rates from time-dependent luminance data is described in more detail. Ordinarily, it will be possible and optimal to use the data from 0–3 or 1–3 minutes after reaction initiation for linear regression, since little or no saturation is usually evident in this time range unless the signal is extremely strong. However, when the user is dealing with samples about which very little is known, which may contain very large numbers of cells or an unexpectedly large proportion of dead cells, it is possible that the linear range of the assay will be exceeded even in this timeframe. One method of dealing with this potential problem is to select a useful time range of data and perform linear regression only within that time interval, but the selection of an appropriate range may be problematic, time-consuming, or subjective. The software provided as part of Example 3, including appendices 1, 2, and 3 (provided under a separate protective cover), provides a solution to this problem by analyzing every possible sequence of four or more consecutive data points within the data-set and selecting the time range with the highest coefficient of correlation. The program then reports the linear fit for that optimal time range, the correlation obtained for that fit, and the actual timepoints that were used. Appendix 1 is the program listing as an Excel macro. Appendix 2 is a sample input data file, and Appendix 3 is the resultant output, showing the best correlation coefficient for each data set, the linear fit of the chosen range ("rate"), and the data range chosen (labeled "notes"). It will be evident to one skilled in the art how to extend this program to a data-set larger than ten timepoints. Simple modifications to this program would allow the user to perform manipulations over all samples at once. For example, the program could be modified to choose the most linear range from a particular standard or calibration sample (or the average of a subset of the samples) and calculate the rate using that same time range for all the samples. Alternatively, it will be evident to one skilled in the art that a closely related procedure could find a time range which yielded the best minimum correlation over the entire sample set and applied that time range to all samples. These latter methods have the advantage that the same time range is used for all samples. Moreover, various warnings could be added to the code, such as "no good fit exists," "data non-monotonic," "slope outside expected range" (especially for standards and calibrators), "lag phase encountered," or "saturation reached."

In another aspect, the present invention provides methods and compositions for measuring bacteriolysis. This is shown in Example 4. The combined cytotoxicity/proliferation mode is shown in use with bacteria under Example 8.

In another aspect, the present invention provides methods and compositions for measuring cytotoxicity and/or proliferation by means of combinations of enzymes other than those shown in FIG. 1. As an example, the Aldolase-DeathTRAK reaction is similar to the DeathTRAK reaction, but glyceraldehyde-3-phosphate is generated in situ by the action of aldolase on fructose-1,6-bisphosphate, rather than being provided in the cocktail as it is in DeathTRAK. Example 5 demonstrates the use of this alternative assay and shows the general applicability of the coupled-luminescent concept to various enzyme combinations, as discussed further under Example 14.

In another aspect, the present invention provides methods and compositions for measuring cytotoxicity of a compound, mixture of compounds, cell or cell fragment, virus or viral fragment, organism or organismal fragment, radiation, physical or mechanical stress, or any other substance, process, or combination of these. In general the cytotoxic or damaging effects of substances or processes that are compatible with a liquid phase can be measured in the same manner as in Example 1. The DeathTRAK assay, Aldolase-DeathTRAK assay, and other coupled luminescent systems as exemplified below are compatible with a wide range of substances, buffers, lytic agents, and cell types. Example 6 describes the general case of measurement of cytotoxicity or membrane damage induced by a "cytotoxic agent," which may be any of the entities listed in this paragraph.

In another aspect, the present invention provides methods and compositions for measurement of cell proliferation (see Example 7). These methods involve either killing of all the cells or introduction of a substance or process which induces release of G3PDH from the cells, accompanied by a Death-TRAK assay or one of the other coupled luminescent assay types described under Example 14.

In a preferred mode of use, the present invention provides methods and compositions for measuring both cytotoxicity and proliferation (or viability) of a single sample. This involves a combination of the methods described under Examples 6 and 7. The combined method is described in Example 8, including experiments with both mammalian cells and bacteria.

In another aspect, the present invention provides methods and compositions for high-throughput screening for cytotoxicity and/or membrane damage and/or proliferation (Example 9). The cytotoxicity/membrane damage may be desirable (as in screening for drug candidates with activity against a given cell type, such as a cancer cell or infectious organism) or undesirable (as in screening lead compounds or libraries for undesirable effects).

In another aspect, the present invention provides methods and compositions for screening for drug sensitivity and drug resistance (Example 10). These methods may be used, for example, to aid decisions as to treatment strategy for a patient who is suffering from cancer or an infectious disease.

In another aspect, the present invention provides methods and compositions for research into and/or measurement of apoptosis (Example 11).

In another aspect, the present invention provides methods and compositions for testing for the presence of live cells in cases where sterility or a low bioburden is desirable (Example 12).

In another aspect, the present invention provides methods and compositions for environmental toxicity testing (Example 13).

In another aspect, the present invention provides methods and compositions for extension of coupled luminescent assays to other enzyme systems (Example 14).

In another aspect, the present invention provides methods and compositions for extension of coupled luminescent assays to applications other than cytotoxicity and proliferation (Example 15).

In another aspect, the present invention provides methods and compositions for quantifying free phosphate. In a second preferred mode, the total quantity, total change, or rate of change in the amount of free phosphate is used as an indication of the activity of a phosphatase or phosphatases, and may be used in screening for inhibitors or other modulators of phosphatase activity (Example 16).

In another aspect, the present invention provides alternative applications for measurement of free phosphate as described in Example 16. These alternative applications are described in Example 17.

In the examples described further below, assays with specific parameters are exemplified. However, the present invention provides a set of methods and compositions for coupled luminescent assays using various concentration ranges of the chemical and biochemical components specified for the DeathTRAK assay described herein, such that the assay functions with the following concentrations:

Dithiothreitol (DTT): 0–20 mM final concentration

Adenosine diphosphate (ADP): 0–1 mM final concentration

Alternatively, ultrapurified ADP: 0–1 mM final concentration

Nicotinamide adenine dinucleotide, oxidized form (NAD+): 0.1–50 mM final concentration Glyceraldehyde-3-phosphate: 1 µM-100 mM final concentration Triethanolamine: 0–1 M final concentration Sodium phosphate: 0.1 mM to 1 M final concentration Ethylamine diamine tetraacetic acid: 0–50 mM final concentration Bovine serum albumin: 0–20 mg/mL final concentration ATP assay cocktail: 1–85% final concentration ATP assay diluent: 0–90% final concentration Phosphoglycerokinase (PGK): 1 in $10^{11}$ parts to 1 in $10^5$ parts final concentration (beginning with stock solution at approximately 5000 units per mL)

Alternatively, ultrapurified PGK: 1 in $10^{11}$ parts to 1 in $10^3$ parts final concentration (beginning with stock solution at approximately 5000 units per mL)

IMDM-0–801% of the final reaction volume

PBS-0–80% of the final reaction volume

As explained herein, data may be obtained from the DeathTRAK assays and other assays based on the coupled luminescent principle at a single timepoint, at multiple individual timepoints, or as a time-linear fit of luminance data. The readout may be taken as soon as 1–2 seconds after injection, or as long as 24 hours after injection. DeathTRAK and other assays based on the coupled luminescent principle may be run at any temperature from just above freezing (0° C.) to approximately 60° C. Reaction cocktails and other components of DeathTRAK and other assays based on the coupled luminescent principle may be stored under a variety of conditions. In some cases the user may decide to use given storage conditions for convenience with full knowledge that part of the activity may be lost, since the sensitivity of the assay methods is so great that the remaining activity may be sufficient for many uses. The DeathTRAK reaction cocktail may be stored at room temperature for up to 12 hours, at 4° C. for up to 7 days, or at −15° C. or lower temperatures for up to five years. If the luciferase (ATP assay cocktail) component is kept lyophilized at −15° C. or colder and the PGK component is stored separately at 4° C., the reaction cocktail may be stored at 4° C. for up to one year.

The user has the option of using various types of microplates for obtaining luminance readouts. For example, standard luminance plates (black, white, mixtures of colors, or clear multi-purpose plates), tissue-culture plates, fluorescence plates, or EIA plates may be used. In contrast to methods that do not yield strong signals, the sensitivity of the coupled luminescent assay methods described herein is such that the signal obtained from all of these types of plates will be sufficiently strong for many uses. In particular, the cytotoxicity/proliferation dual mode experiments shown in Example 8 were carried out in standard white luminance plates. The cells were seeded directly into the plates, and no further processing was needed prior to addition of the toxins under study the following day.

The following examples are offered by way of illustration and not by way of limitation.

Chemicals and biochemicals were purchased from Sigma-Aldrich (St. Louis, Mo.). Growth medium (IMDM) was purchased from Irvine Scientific Corporation (Santa Ana, Calif.).

EXAMPLE 1

Measurement of a Cytolytic Process by DeathTRAK

The unoptimized DeathTRAK assay cocktail was used to measure the effect of an anti-Factor I antibody on complement-mediated lysis of the PC-3 prostate-cancer cell line. Cells were grown in Iscove's Modified Dulbecco's Medium (IMDM) with 10% fetal bovine serum, then treated with 0.25% trypsin/EDTA to allow removal from the growth flask, and subsequently washed with IMDM to remove trypsin and EDTA. Assays were performed in triplicate. Since complement requires some time to act against its target, the cells were incubated with complement serum and other components (see composition below) for 100 minutes at 37° C. in a covered Costar low-binding plate (Cat. #3596) before the data in FIG. 5 were taken. A 0.005-mL aliquot of each complement reaction was then transferred to wells of a microtiter plate, along with a control using complement that had been heat-inactivated at 60° C. for two hours. Because the DeathTRAK cocktail is compatible with live cells, it was not necessary to remove the cells or otherwise treat the reaction mixture prior to the cytotoxicity assay. The microtiter plate was transferred to the luminometer. Each well was injected with 0.045 mL of reaction cocktail (composition below). The no-complement rate has been subtracted from each data-point on both charts. The averages of three runs are shown.

Several conclusions are evident from the data. First, in spite of the difference in the scales and the fact that FIG. 5 reports a rate of change of luminance, while FIG. 6 reports an absolute luminance, the two figures appear to show almost identical phenomena. This means that almost all of the accuracy and information of obtaining linear fits from the 20-minute run is captured in a 2.6-minute run with a single readout. This is a general phenomenon, and single-point readouts after an interval of 1–3 minutes are very useful, as long as automated injection is used. However, if the reagent cocktail is loaded manually, then the interval between the initiation and the luminance read will not be the same for each sample, and absolute luminance readouts will not be useful. Instead, the user would take a linear fit, typically of the data from approximately 1–3 minutes of the reaction. This yields a rate of increase of the luminance signal, which eliminates the effect of the variations in intervals between initiation and readout among the samples. In general, in the high-throughput setting, the reagent cocktail is injected automatically, and single-point reads will yield excellent results. The standard deviations of the triplicate runs are small in each case and are actually smaller in the single-point data. Finally, both runs show the anticipated effects, including the fact that complement alone has a small effect without antibody (zero-antibody point), but the antibody greatly enhances complement-mediated killing at 10–30 nM.

TABLE I

Complement Lysis Mixture Composition

| Material | Percentage |
|---|---|
| IMDM | 9.6% |
| Mg-EGTA | 3% |
| Human complement serum | 40% |
| PC-3 cells (1000,000/mL) in IMDM | 45% |
| PBS, with or without anti-Factor I monoclonal R65 | 2.4% |

The Mg-EGTA component was made up as follows:
  300 mM magnesium chloride and 200 mM ethylene glycol tetraacetic acid in $H_2O$, brought to pH 7.5 with NaOH and pass through a 0.22-micron filter.

Figure 5:
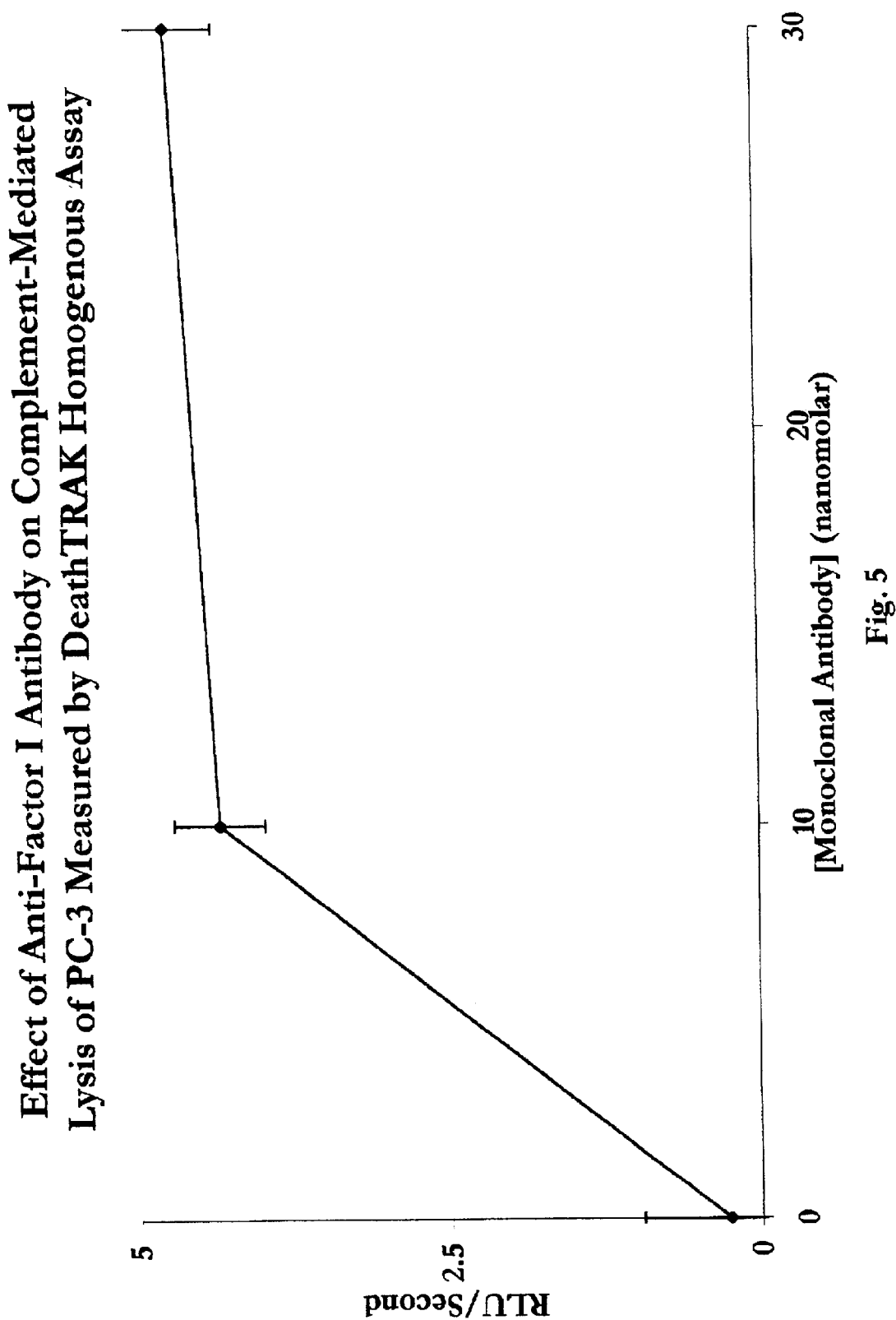
FIG. 5 shows the results of enhancement of complement-mediated killing of the prostate cancer cell line PC-3 by an anti-Factor I antibody, as measured by the DeathTRAK homogeneous assay. The units of the Y axis are Relative Luminance Units/Second; the Y values were obtained by linear fits of the luminance data against the time that each luminance reading was taken (compare FIG. 6).
Figure 6:
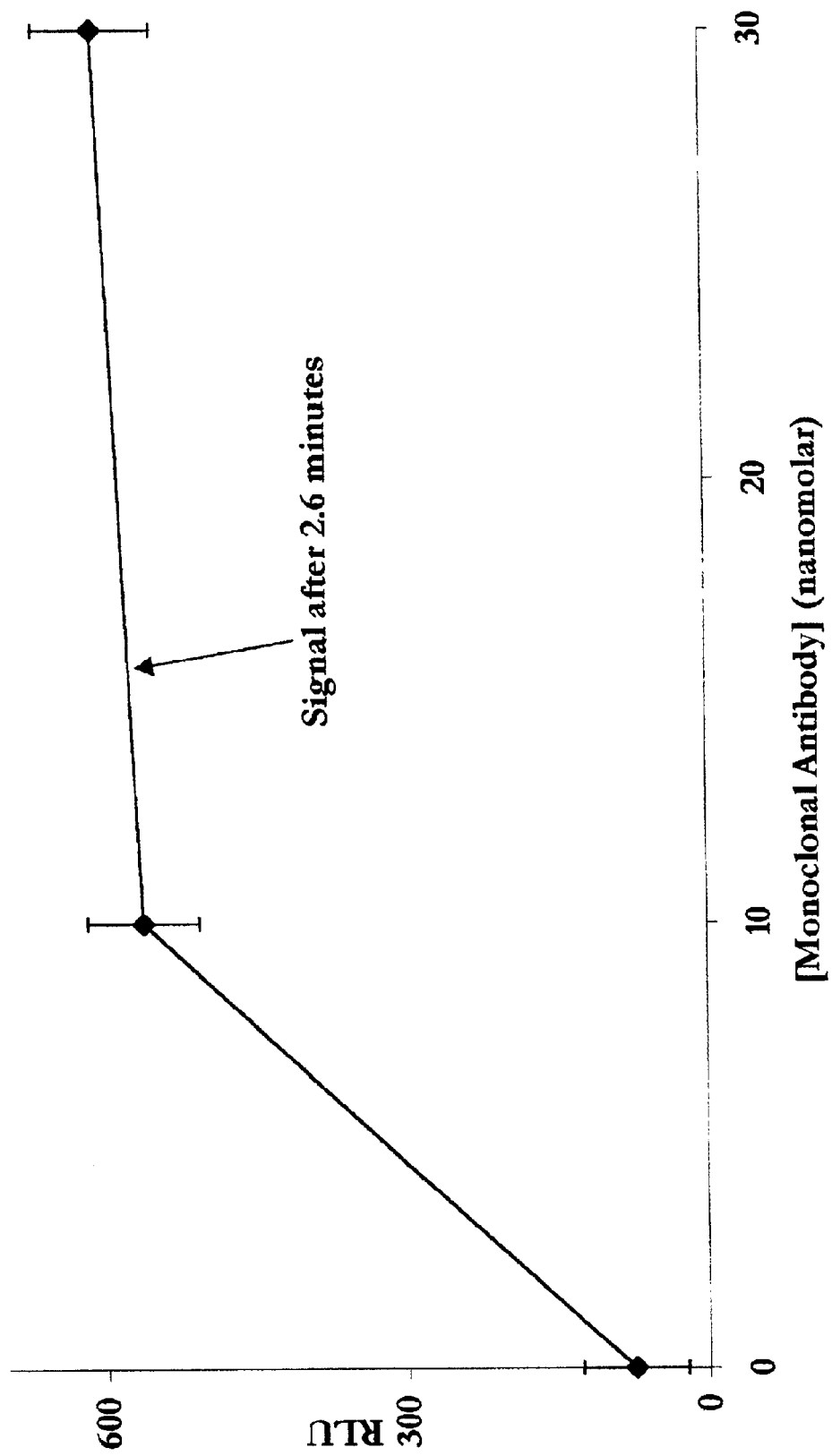
FIG. 6 shows the results of the same experiment as FIG. 5, using only a single data-point from each reaction for the analysis. The units of the Y axis are therefore Relative Luminance Units, reflecting an absolute luminance at a point 2.6 minutes into the DeathTRAK assay.

0.005 mL of the lysis reactions was removed and mixed with 0.045 mL unoptimized DeathTRAK cocktail (0.25 mL 4×GP cocktail, 0.125 mL ATP assay reagent, 1.125 mL ATP assay diluent, 2.3 mL IMDM containing 10% fetal bovine serum, 0.0025 mL 1:1,000,000 PGK in PGK diluent). Thus this assay was not performed in homogeneous mode. Example 2, below, explains how the reagent cocktail was formulated and optimized for homogeneous mode. The wells were read for luminance for 1 second immediately after injection, and subsequently every 150 seconds for a total of 20.1 minutes (1205 seconds). The timepoints from 305 to 1205 seconds were taken for data reduction by linear regression, using Microsoft Excel (FIG. 5). In addition, single timepoints after 155 seconds of incubation were taken as endpoints for comparison (FIG. 6).

The 4×GP cocktail was made as follows:
  10 mL 5× PGK diluent
  0.05 mL 1M DTT
  0.00295 mL 100 mM ADP
  0.5 mL 100 mM NAD+
  0.52 mL glyceraldehyde-3-phosphate (49 mg/mL as purchased)
  1.425 mL $dH_2O$ The 5× PKG diluent was made as follows:
  3.73 g of Triethanolamine (TEA)=25 mM
  1.5 g $NaH_2PO_4$
  1.295 mL 193 mM Ethylene Diamine Tetraacetic Acid (EDTA) pH 8.0
  25 mg Bovine Serum Albumin (BSA) Fraction V
  Titrated to pH 7.0 with concentrated HCl and made up to a final volume of 50 mL.

PGK diluent (1×) was made up by diluting one part of 5× PGK diluent with four parts deionized $H_2O$.

EXAMPLE 2

Improved Measurement of G3PDH Activity and/or Cytolysis and/or Membrane Damage by Optimize DeathTRAK This example demonstrates the process of developing the method into a homogeneous assay suitable for use in high-throughput screening. This includes: Example 2A, in which the cocktail is optimized for signal strength while maintaining compatibility with live cells; Examples 2B and 2C, in which the PGK and ADP concentrations, respectively, are optimized; Example 2D, in which the optimized cocktail is tested for linearity and dynamic range; Examples 2E and 2F, in which the storage conditions are tested and optimized; Example 2G, which shows the advantages of protecting the DeathTRAK cocktail from light or adding the PGK component shortly before reaction initiation; and Example 2H, in which the use of a stop reagent is demonstrated.

EXAMPLE 2A

Titration for Optimum Ratio of IMDM to PBS at Low Signal Strength

In this Example, the concentrations of PBS and IMDM, both of which are cell-compatible buffers, were varied inversely in order to determine the optimum composition for cell compatibility and high signal strength. A cocktail was made consisting of 0.114 mL 4×GP cocktail, 0.057 mL ATP assay cocktail, 0.513 mL ATP assay diluent, 0.0011 mL 1:1,000,000 PGK, and 0.00057 mL DTT. 0.0229 mL of this cocktail was distributed to each of 24 wells of a luminescent microtiter plate. 16 wells also received 0.005 mL of 1:100,000-diluted G3PDH, while the other 8 wells received only 0.005 mL G3PDH dilution buffer. The 16 +enzyme wells and the eight −enzyme wells then received amounts of MDM and PBS varying from 0–100% of the 0.0221 mL remaining in the 0.05-mL reaction. The plate was then read for luminance for one second each 60 seconds for 10 minutes. The last seven timepoints were analyzed by linear regression and the duplicate rates (+enzyme only) were averaged. The results showed a broad maximum in activity from 60–100% IMDM and 40–0% PBS (the final concentration range after addition of the other cocktail components and the sample was 26.544.2% IMDM and 17.7–0% PBS). Any concentration ratio in this range may be used.

Composition of the G3PDH dilution buffer was:
1000 parts PGK diluent
1 part 1M dithiothreitol

EXAMPLE 2B

Optimization of PGK Concentration

The assay suffered from poor linearity, especially with [G3PDH]. It was hypothesized that a deficit of phosphoglycerokinase (PGK) was causing this problem. There are both upper and lower constraints on the concentration of this enzyme, because the commercial preparation typically comes with some contaminating G3PDH, which causes dynamic background. The following experiment was used to optimize the PGK concentration for use in the rapid, homogeneous format.

0.483 mL IMDM 0.2535 mL PBS 0.127 mL 4×GP cocktail 0.0633 mL ATP assay cocktail 0.5703 mL ATP assay diluent 0.0006 mL 1M DTT 0.2488 mL of this cocktail was aliquoted into each of five reaction vessels, which received 0.00125 mL of varying dilutions of PGK:

| Vessel | 1 | 2 | 3 | 4 | 5 |
|---|---|---|---|---|---|
| PGK Dilution | $3 \times 10^{-6}$ | $1 \times 10^{-5}$ | $3 \times 10^{-5}$ | $1 \times 10^{-4}$ | $3 \times 10^{-4}$ |

The contents of each reaction vessel were aliquoted in duplicate onto a microtiter plate. A fixed amount of 0.005 mL of 1:10,000-diluted G3PDH was added in duplicate to each PGK dilution and the reactions were read for luminance. The results showed that PGK diluted $1 \times 10^{-4}$ from the purchased reagent yielded an excellent signal, although saturation was seen, which proved to be due to exhaustion of ADP. Still higher concentrations of PGK led to sublinear behavior even after the ADP concentration was adjusted (see Example 2C, FIG. 7). This concentration of PGK ($1 \times 10^{-4}$) was therefore selected for the optimized cocktail. However, since the level of G3PDH contamination in a different lot of PGK could be higher, it may be necessary to test each lot for this problem when in commercial production. If the G3PDH contamination is unacceptably high, another source can be found, or the PGK enzyme can be purified away from G3PDH, or labile, irreversible inhibitors of G3PDH such as iodoacetic acid can be used to inactivate the contaminant.

EXAMPLE 2C

Adjustment of ADP Concentration

The saturation seen after PGK optimization was likely to be due to exhaustion of a consumable component from the reaction. ADP was a candidate component because the concentration of ADP that can be used is limited by the fact that commercial ADP preparations are contaminated with ATP, which increases the static background.

Figure 7:
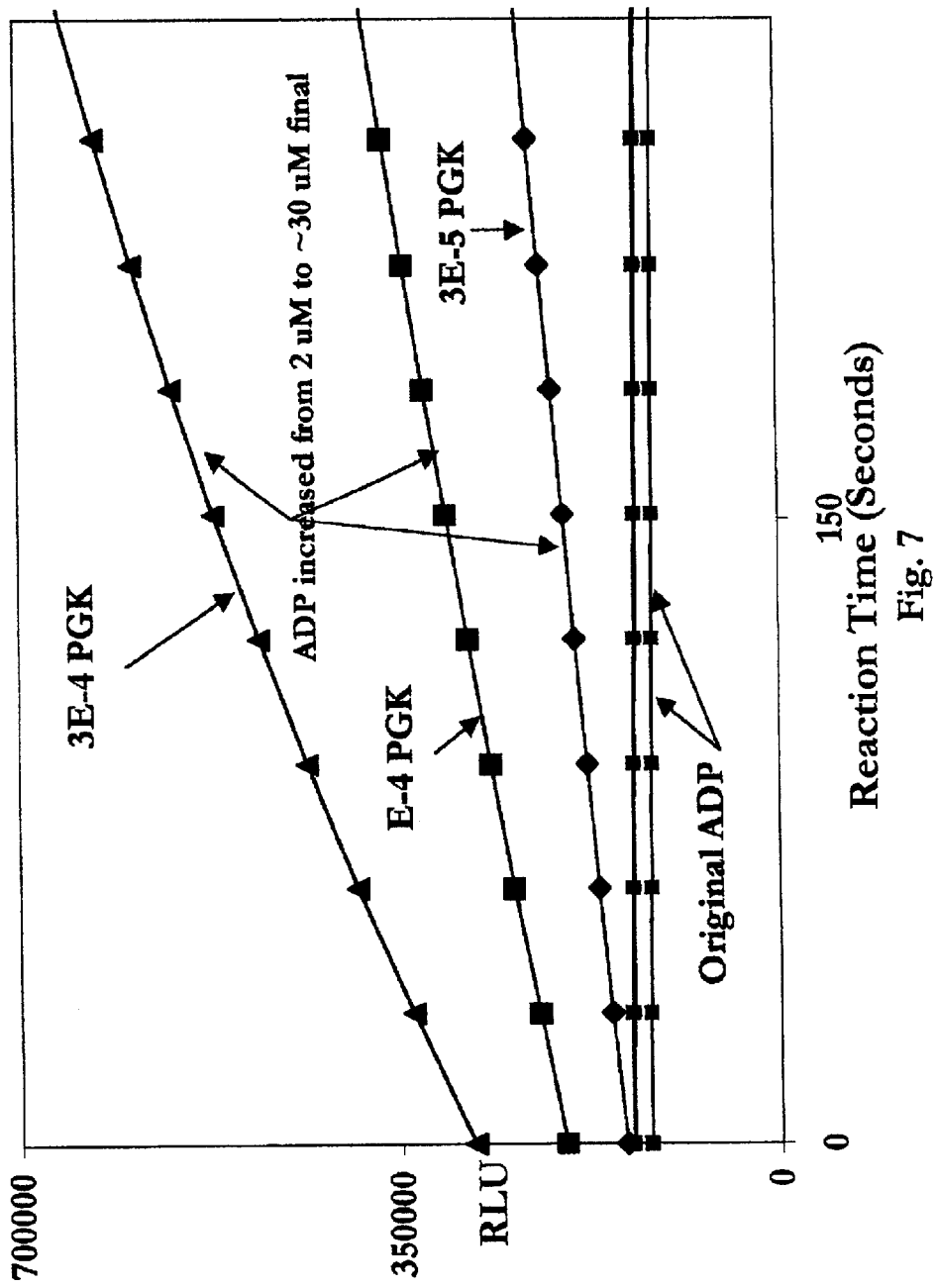
FIG. 7 shows the effect of additional adenosine diphosphate (ADP) on the response of the DeathTRAK homogeneous cocktail. ADP was added to three reactions, with various concentrations of PGK. Controls (marked "Original ADP") had the same concentrations of PGK but received no additional ADP.

In this experiment, ADP was increased from 2 $\mu$M (original) to 30 $\mu$M after the reactions described in Example 2B had been running for 2.4 hours, and luminance was read. ADP was clearly limiting in all three reactions, and the addition of ADP to the reactions with optimized PGK led to a rate of over 1600 RLU/sec with almost no loss in linearity ($R^2 > 0.999$) over the first 150 seconds (FIG. 7). Before addition of ADP, the reactions were reaching saturation at ~160,000 RLU, but in the experiment depicted in FIG. 7, there was little deviation from linearity, even at 600,000 RLU. The composition of the new optimized cocktail was (2.9974 mL final volume):

TABLE II

Composition of Optimized DeathTRAK Cocktail

| Material | Amount (for 2.9974 mL Final Volume) |
|---|---|
| IMDM | 0.936 mL |
| PBS | 0.507 mL |
| $10^{-4}$ diluted PGK | 0.0025 mL |
| 4XGP cocktail | 0.2535 mL |
| ATP assay cocktail (freshly dissolved) | 0.1266 mL |
| ATP assay diluent | 1.1406 mL |
| 1M dithiothreitol | 0.0012 mL |
| 2.8 mM adenosine diphosphate | 0.03 mL |

EXAMPLE 2D

Tests of the Optimized Cocktail

The optimized cocktail was also tested with the G3PDH test enzyme by dilution over two orders of magnitude, yielding a linear correlation of >0.9998, with coefficients of variation of individual points ranging from 3–6%.

The optimized cocktail was also tested against another method of determining cytotoxicity. FIG. 3 shows a comparison of DeathTRAK results with an independent, "blinded" estimate of killing by a cell-culture technician visualizing the cells through a microscope. The close correlation of 0.990 demonstrates, first, that the maximum DeathTRAK signal corresponds to death of all the cells, and second, that the DeathTRAK method agrees well with another technique. Of course direct visualization is too labor-intensive to use on a regular basis. The methods used were the same as those used for the 841CON and PC-3 cell lines in the experiments reported under Example 8, except that the total-lysis step was not performed.

The optimized DeathTRAK cocktail was also used to test sensitivity and linear response to dead Raji cells. Non-adherent Raji cells were harvested, resuspended at the same concentration (300,000/mL) in Lysis Buffer B (Lys.B, Phosphate buffered saline plus 1% Nonidet P40), and incubated for 10 minutes at room temperature to kill them. They were then serially diluted with Lys.B to yield the indicated numbers of cell equivalents per mL. 0.005 mL of each dilution in triplicate was mixed with 0.045 mL of optimized DeathTRAK cocktail and luminance was read for I second every 60 seconds for ~720 seconds. The dose-response curve of the assay over four orders of magnitude is shown in FIG. 4.

EXAMPLE 2E

Optimization of Storage Conditions

Full and Partial Cocktails, Lyophilization vs. Freezing

In this experiment, the unoptimized cocktail (see Example 1) was made up with or without various components and frozen at $-80°$ C. or lyophilized; the aliquots were then thawed or reconstituted and tested with PC-3 cells. Tube 1 contained the full cocktail; tube 2 contained everything except PGK; tube 3 contained everything except PGK, ATP assay cocktail, and ATP assay diluent; tube 4 contained the 4XGP cocktail only. Each of these 4 tubes contained enough constituents to make up 3 mL final of the cocktail. The contents of each of the 4 tubes were aliquoted into 5 storage tubes each (containing enough constituents for 0.5 mL final of the cocktail). The 5 tubes of each set were treated as follows: aliquot 1 was lyophilized and stored frozen (−20° C.) for 1 day; aliquot 2 was lyophilized and stored at room temperature for 1 day; aliquot 3 was lyophilized and stored frozen (−20° C.) for 4 days; aliquot 4 was frozen immediately (−80° C.) and stored for 1 day; aliquot 5 was frozen immediately (−80° C.) and stored for 4 days. Because the final cocktail is approximately 33.8 mM in TEA, this amount of TEA was added to the lyophilized aliquots for reconstitution.

The aliquots were tested in duplicate (0.045 mL each) with 0.005 mL of PC-3 cells killed by diluting 1:100 into Lys.B. (final 3000 cells/mL). Linear fits were taken of the luminance reaction. After 4 day's storage, room temperature had completely killed the reactions with ATP assay cocktail present and destroyed most of the activity even with the ATP assay cocktail stored separately. Lyophilization was also clearly inferior to freezing. Subsequently tests with the optimized cocktail showed that the best and most convenient storage method was to make the non-labile cocktail described below under Example 8 and store it separately at −20C or −80C, adding the ADP (stored at −20C or −80C), PGK (stored at +4C), and ATP Assay (stored at −20C or −80C) components either on the day of use or immediately before use.

EXAMPLE 2F

Stability of the Full Cocktail
Effects on Static Background of Freezing vs. 4° C.

In formulating a homogeneous assay it was necessary to determine not only how well the assay activity would survive storage, but also how the static background would be affected (the dynamic background is due to enzyme activity and would not be expected to increase upon storage). The fill non-optimized cocktail with or without PGK present was subjected to storage at 4° C. or −80° C. The aliquots were then checked with 0.005 mL Lys.B (containing no cells) for initial luminance value. Storage of the cocktail with or without PGK present made essentially no difference, but storage at −80° C. caused an increase of <30% in the static background, compared to an increase of >1000% at 4° C. This confirmed the benefits of freezing the cocktail components (other than PGK), as mentioned under Example 2E.

EXAMPLE 2G

Figure 8:
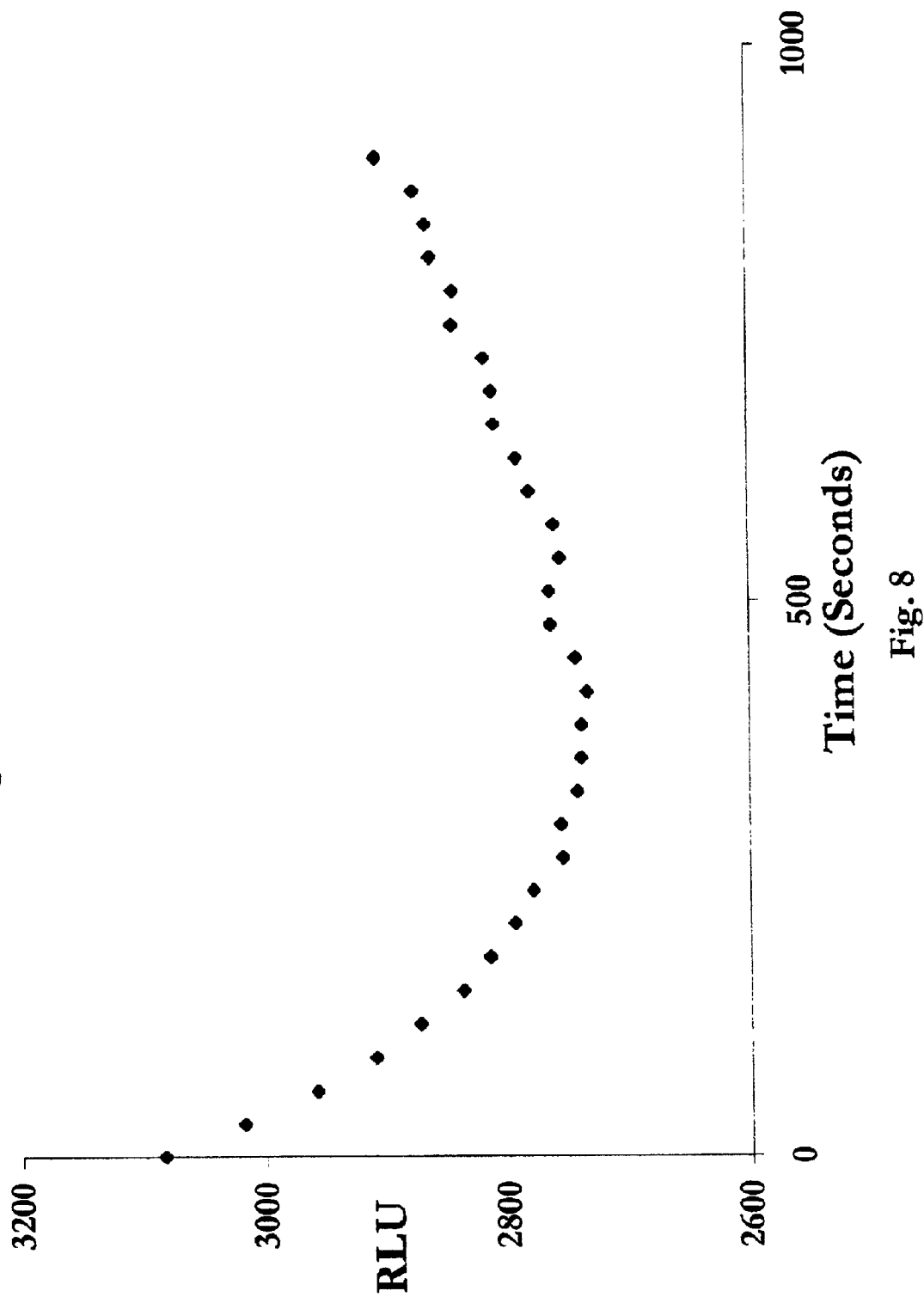
FIG. 8 shows an example of the lag phase, due to extended exposure of the reaction cocktail to light in the presence of PGK.
Figure 9:
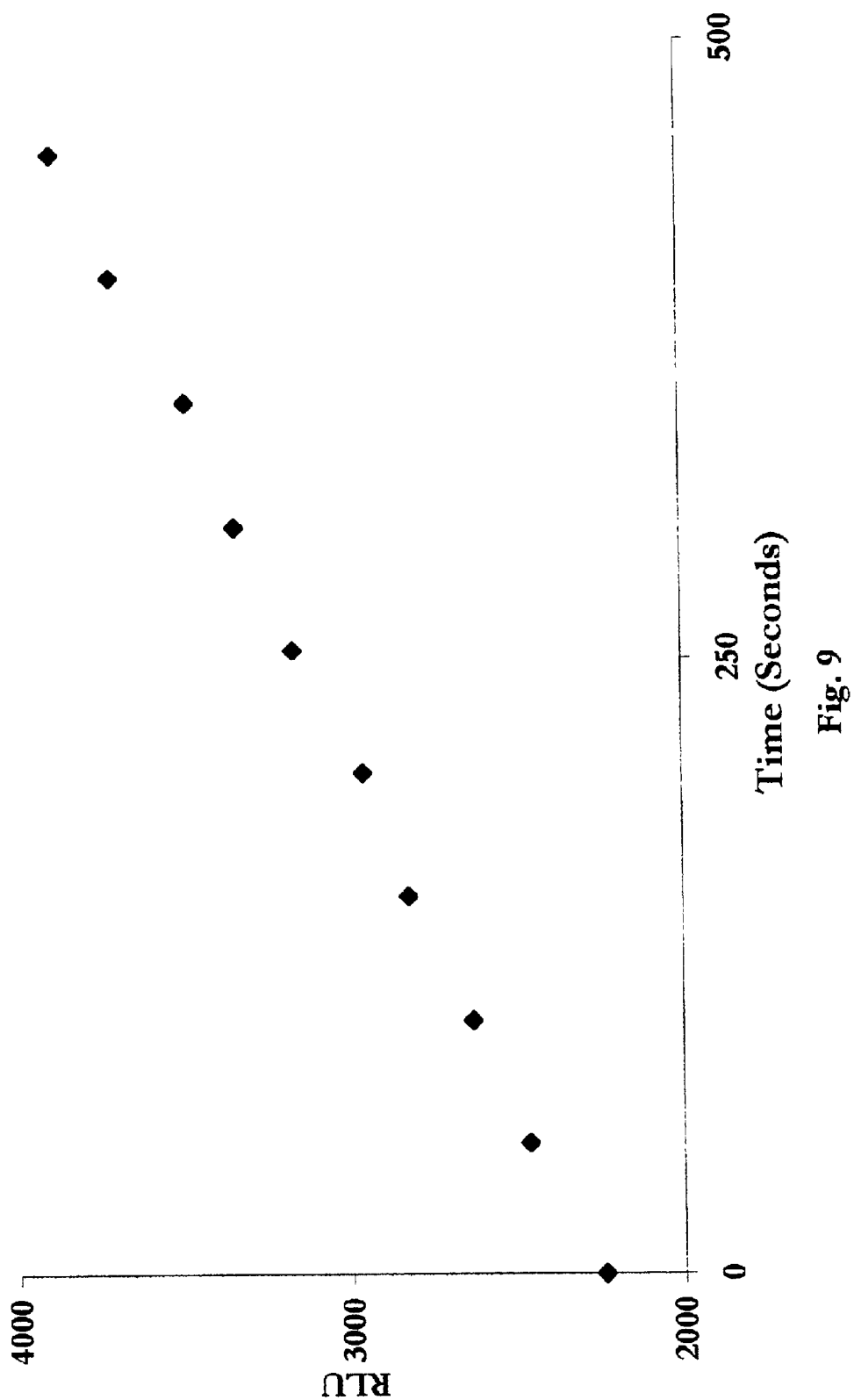
FIG. 9 shows an example of a reaction in which precautions were taken to eliminate the lag phase.

Elimination of lag Phase by Protecting Cocktail from Light After Addition of PGK FIG. 8 shows an example of a reaction in which the cocktail was not protected from light for a substantial period of time after addition of PGK. If the assay is run within a few minutes after addition of PGK, the lag phase is not seen, but if a significant amount of time elapses after addition of PGK, then the small amount of G3PDH enzyme contaminating the PGK preparation causes a slow accumulation of ATP. This ATP reacts with luciferase to generate light, adenosine monophosphate (AMP), and inorganic pyrophosphate ($PP_i$), but also in the presence of light, the backward luciferase reaction is also possible, ie., AMP, $PP_i$, and light can be combined by luciferase to make ATP. Because of these reactions, a steady-state level of ATP is achieved. When the plate is then transferred to the interior of the luminometer, which is completely dark, the backward reaction becomes impossible. As a result, the extra ATP present is rapidly broken down by luciferase, leading to a rapidly declining signal during the first 5–10 minutes of the reaction. Eventually, the extra ATP is exhausted, and the normal, linear signal due to the G3PDH in the test sample is revealed. To avoid this problem, the user needs to prevent the ATP level in the cocktail from rising. This is accomplished either by withholding the PGK component until shortly before the reaction is initiated, or by protecting the cocktail from light. The latter method is more suitable for a high-throughput screening environment, in which a timed addition of a reagent to the cocktail prior to each run is inconvenient. Under these circumstances the reagents can be mixed and kept in an opaque or dark-glass bottle. Even if the cocktail was exposed to light during the process, the steady-state level of ATP will decline to an acceptable value after the cocktail is shielded from light. FIG. 9 shows the results of a run in which the cocktail was protected from light after addition of PGK. There are no substantial deviations from linearity in the run.

EXAMPLE 2H

Use of Stop Reagent

To demonstrate the use of a stop reagent, DeathTRAK reaction cocktail was made as for Example 1. To a 0.5-mL aliquot of this cocktail, 0.0016 mL of 1:1,000,000-diluted PGK were added (termed "+PGK" cocktail). Two 0.045-mL aliquots of the standard unoptimized cocktail and two 0.045-mL aliquots of the "+PGK" cocktail were measured into a luminescent microtiter plate. 0.005 mL of 1:100,000-diluted G3PDH was transferred to each of these four aliquots of cocktail. After 21 minutes' incubation at room temperature, 0.02 mL of 20 mM bromopyruvic acid (BPV) dissolved in ATP assay diluent was added to one reaction with the unoptimized cocktail and one reaction with the "+PGK" cocktail 0.020 mL of ATP assay diluent alone was added to the other two reactions. This quantity of BPV (~3 mM final) stopped the increase in luminance in the reactions both with and without added PGK. In fact there is a small negative rate of change of luminance in the stopped reactions, but this is likely to be due merely to exhaustion of ATP by luciferase. Use of this or an alternative stop reagent allows the user to delay reading the plate, while maintaining the relative signal strengths of the samples.

EXAMPLE 3

Software for Analysis of DeathTRAK Data

An Excel macro was written which seeks the best linear fit of four or more consecutive timepoints for each well and reports the rate calculated from the fit, the correlation coefficient, and the identity of the time range that yielded the best fit. Currently the macro also outputs all of the fit rates and correlation coefficients onto the spreadsheet, but this could easily be switched off. At present the macro has a limitation of 10 timepoints for each well, but it would be evident to one skilled in the art that this can be increased. Documents provided are Appendix 1 (the macro code), Appendix 2 (a sample input file to the macro) and Appendix 3 (output of the macro from the sample input file).

Appendix 1 is a printout of the "fitfinder" Excel macro (program) which accepts input in the form of luminance (or other) time-dependent data in a practically unlimited number of samples, identifies the time range which yields the best linear fit (i.e., the highest correlation coefficient), and reports the correlation coefficient, fitted slope, and time range used. Appendix 2 is an example of a luminance run with the DeathTRAK homogeneous assay which was used as input to the macro. Appendix 3 is a printout of the output of the "fitfinder" macro, given the input of Appendix 2. In addition to the reported correlation coefficients, slopes, and time ranges (near the beginning of the appendix), tables of all the slopes and correlation coefficients used for the calculations are displayed in the lower part of the appendix.

EXAMPLE 4

Measurement of Bacteriolysis by DeathTRAK

Figure 10:
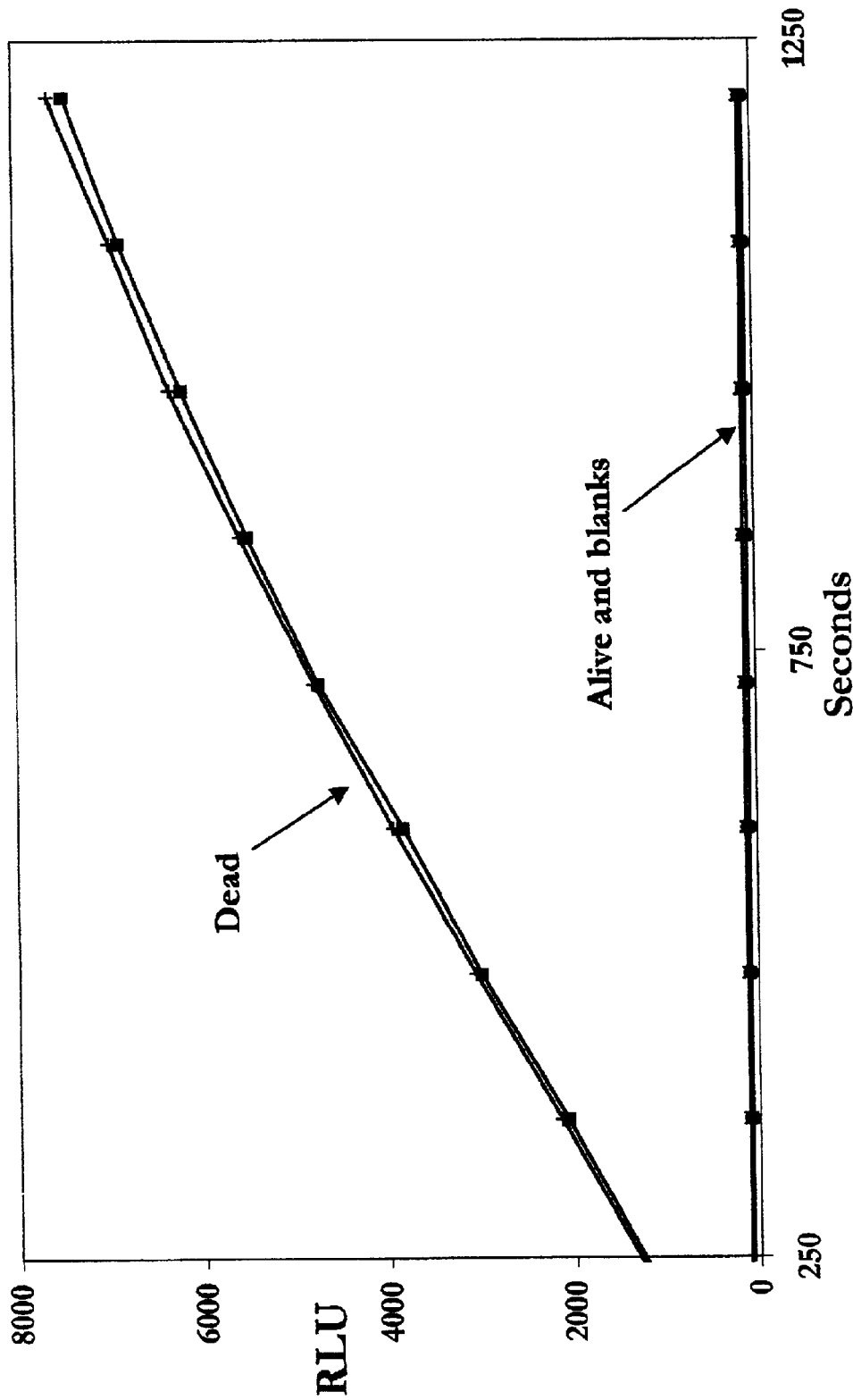
FIG. 10 shows a cytotoxicity assay in which live or dead *E. coli* cells (strain EV-5) were diluted directly from culture and mixed with the DeathTRAK homogeneous cocktail. Data from duplicate runs are shown.

E. coli strain EV-5 was lysed by resuspension in Somatic Cell ATP Releasing Reagent (SCARR, from Sigma-Aldrich). Bacteria grown overnight in LB were washed twice with PBS and resuspended in the same volume of PBS. Cells were then diluted 1:100 into SCARR and incubated for ten minutes at room temperature. Cells were either used from this mixture or further diluted 1:100 into PBS. Live cells were diluted directly into PBS. The quantity of dead cells was measured by adding 0.005 mL of the suspension or a 1:100 dilution of the suspension in PBS to 0.045 mL reaction cocktail (composition below) and reading the luminance for two seconds every two minutes for 20 minutes. FIG. 10 shows progress curves taken with duplicate 1:100 dilutions of the dead EV-5 cells vs. the same dilutions of live cells and blanks with no cells. The signal associated with the dead cells is very strong, linear, and highly reproducible (both runs are shown). Live cells gave a very faint signal: a 1:10,000 dilution of dead cells gives a very similar signal to a 1:100 dilution of live cells, indicating that leakage from live cells yields about 1% of the signal of dead cells. Composition of Reaction Cocktail 0.09 mL 4XGP 0.0009 mL 1:1,000,000-diluted PGK 0.07 mL PBS 0.3325 mL ATP assay diluent 0.0175 mL ATP assay cocktail

EXAMPLE 5

Aldose-DeathTRAK

In an alternative embodiment of the invention, the G3P component is omitted from the cocktail and two reagents are substituted fructose-1,6-bisphosphate (FBP), and aldolase (the enzyme which cleaves FBP to G3P, which is converted by G3PDH to the substrate for PGK, and dihydroxyacetone phosphate, which plays no role). The formulation of the Aldolase-DeathTRAK cocktail is as follows (5 mL):

0.609 mL 2 mg/mL FBP 0.05 mL 0.1 M DTT 0.00077 mL 38.39 mL ADP 0.005 mL 1:100,000-diluted PGK 0.004 mL 1:1000-diluted aldolase (in PGK diluent)

0.5 mL 10× PGK diluent 3.83 mL dH$_2$O

E. coli strain EV-5 at A$_{600}$ of 0.703 were diluted 1:10 into LB and washed 3× with an equal volume of PBS. Cells were lysed by complement in a reaction of the same composition as that used in Example 1 except that PBS was used instead of IMDM. 0.15 mL of cells were added to 0.15 mL of the reactions containing either active complement (run in quadruplicate) or complement that had been inactivated at 60° C. for two hours (in duplicate). Lysis was measured by removing 0.03 mL of the lysis reaction, centrifuging for 3 minutes at ~1500×g, and transferring 0.01 mL of the supernatant to a luminescent microtiter plate. A mixture of 0.04 mL Aldolase-DeathTRAK cocktail (above) and 0.15 mL ATP assay cocktail diluted 1:20 into ATP assay diluent was then added to each sample. The luminance was read after 23 minutes. Results of duplicate reactions were: +complement, 1.793±0.173 RLU/Sec; –complement, –0.229±0.037 RLU/Sec (p<0.004). The Aldolase-DeathTRAK reaction easily distinguished the effects of active from inactive complement against the E. coli cells.

EXAMPLE 6

Use of DeathTRAK or Another Coupled Luminescent Assay to Measure Effects of a Cytotoxic or Membrane-Damaging Entity The use of DeathTRAK, or another coupled luminescent assay as described below under Example 14, to measure the cytotoxicity of a compound or drug candidate would be similar to its use with complement (Example 1). The Death-TRAK cocktail may be introduced before, during, or after the potentially cytotoxic agent was mixed with the cells, depending on the kind of test being performed. If a quantitative estimate of killing rate were desired, the cells could be mixed with the potentially cytotoxic agent first and incubated for a fixed interval, after which the DeathTRAK cocktail would be added; this would provide an accurate picture of aggregate cell death over time. For maximum speed, DeathTRAK, cells, and the potentially cytotoxic agent could be mixed simultaneously; depending on the speed of killing, a signal could be obtained within minutes, or possibly even less than one minute Finally, mixing DeathTRAK with cells before addition of the potentially cytotoxic agent would allow comparison of the viability before and after treatment. These last two modes would also allow the user to follow the whole toxicity reaction in real time. A calibration standard of cells could be used to obtain absolute quantification.

EXAMPLE 7

Measurement of Cell Proliferation

For a number of uses, it is preferable to measure live rather than dead cells. By doing this, the user can measure effects such as cytostatic and growth-inhibitory behavior, in addition to cytotoxicity. This is often done either with a viability assay that directly measures metabolism (such as Alamar Blue, MTT, or WST) or a method that involves killing all the cells and immediately measuring release of a substance (usually ATP). The problem with the first type of method is that viability assays do not measure the number of live cells at an instant in time, but rather an integral of metabolism over an interval. Also, some of the reagents (such as MTT) have been shown to interfere with metabolism, and/or to be sensitive to redox-active chemicals such as antioxidants. The ATP-release method is destructive but is quite rapid and sensitive. DeathTRAK or another coupled luminescent assay as described under Example 14 is also useful in this mode. The DeathTRAK cocktail may again be added before, after, or simultaneously with the lytic reagent. The luminance readout after lysis and addition of DeathTRAK would correspond with the total cell number. A calibration standard could be used as under Example 6.

Examples of lytic agents for use with various cell types are provided in Example 8. The same lytic agents would be useful if the user desires only a proliferation/viability readout. G3PDH, the enzyme which provides the DeathTRAK readout, is not subject to the same types of metabolic fluctuations as ATP; thus the viability readout of Death-TRAK will often be more closely correlated with cell number than that of the ATP-release assay. A further advantage of DeathTRAK and other methods of the present invention in this mode is that it allows a continuous readout, so that the user can decide to allow the signal to increase further for a later read if desired sensitivity has not yet been achieved. This is not possible with the ATP-release assay.

EXAMPLE 8

Combined Cytotoxicity/Proliferation Mode

In the preferred mode of DeathTRAK use, this Example shows how the information available under both Examples 6 and 7 may be gathered in a single experiment. Death-TRAK or another coupled luminescent assay as described below under Example 14 can be used to measure both live and dead cells in a single reaction vessel. The cocktail is added to the cytotoxicity reaction before lysis and the luminance rate (or a single timepoint) is measured; this represents cells killed by the process under test. A lytic agent compatible with DeathTRAK activity is then added. The rate (or single timepoint) observed after lysis represents the total cell number present (live plus dead). To obtain the number of live cells present before lysis, the signal before lysis is subtracted from the signal after lysis. A calibration standard of cells can be used as under Example 6.

Figure 11:
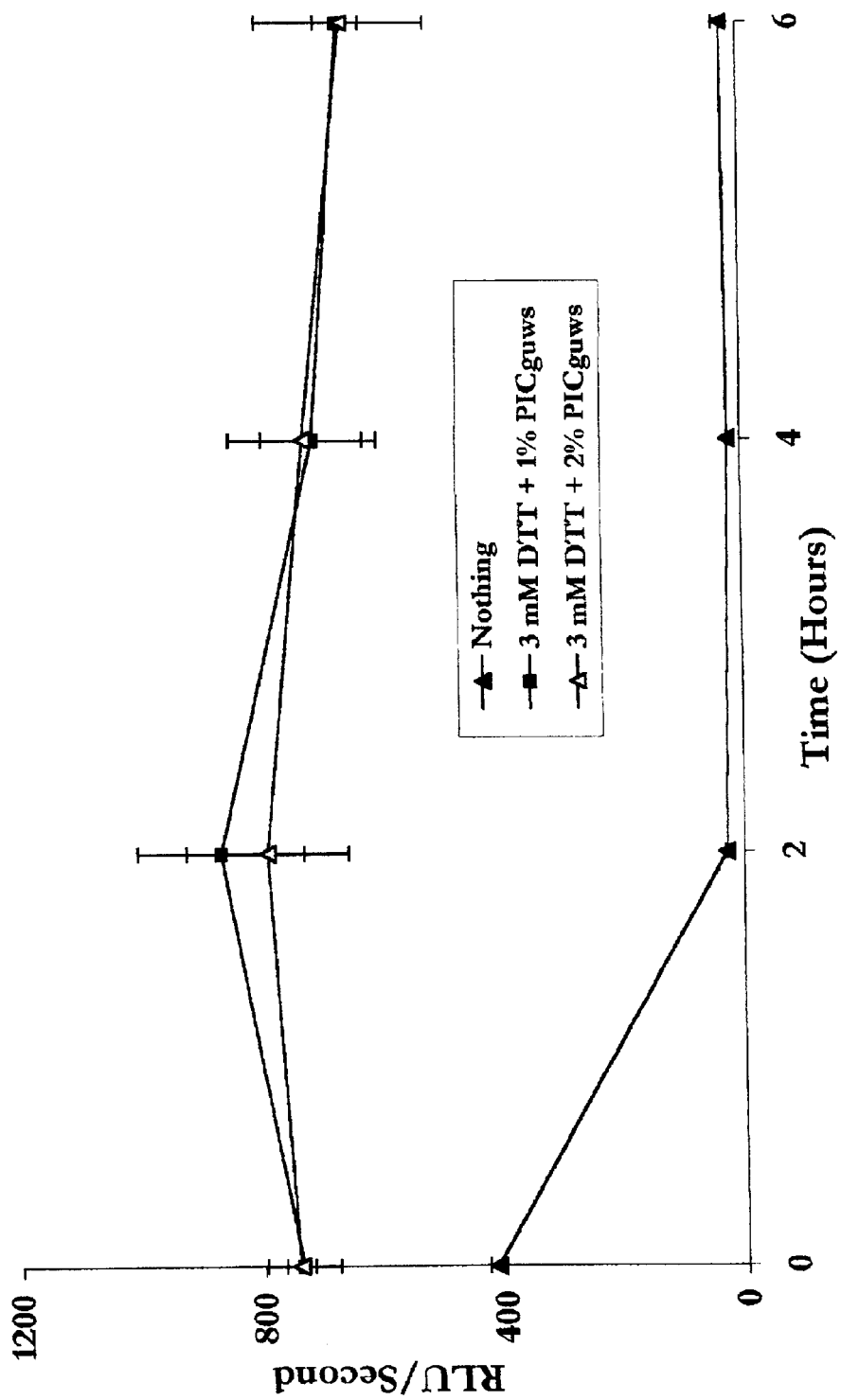
FIG. 11 shows an example of protection of released G3PDH enzyme by a cocktail containing a combination of dithiothreitol and a mixture of protease inhibitors (available from Sigma as catalog #P-2714).

If the user wishes to measure the cytotoxic effects of a given compound, mixture, or biological entity, it may be desirable to incubate the target cells with the potential toxin prior to performance of the assay. While DeathTRAK itself is very rapid, in some cases toxic effects require some time to result in increased release of cellular contents, and/or reductions in cell viability and/or proliferation. During this time, it is possible for some of the possible release enzymes, such as G3PDH in the case of DeathTRAK, to be altered or attacked by the cell environment, or by the aerobic medium in which the cells are growing. FIG. 11 shows that it is possible to protect G3PDH from most or all of the effects of the cellular/growth medium environment by using a judicious mixture of protective agents. In this case the protective agents were 3 mM (final) dithiothreitol, as a reductant, and 1% PICguws, a protease inhibitor cocktail available from Sigma-Aldrich as catalog number P-2714. In these experiments, PC-3 cells were grown to near confluence, trypsinized to resuspend them, and diluted to 20,000 cells/mL in IMDM, with or without 3 mM dithiothreitol and 1% or 2% PICguws. 50-$\mu$L aliquots of this cell mixture were transferred to a luminescent microtiter plate and incubated for the lengths of time indicated in FIG. 11. At the timepoints, 45 $\mu$L of DeathTRAK cocktail was added to triplicate wells and the luminance was measured. Without the protective reagents the G3PDH activity rapidly declines to near zero, but the protective combination leads to very little loss in activity over five hours. In certain cases, one or both of the components of this protective cocktail may be found to interfere with the activity of one or more molecules under test, in which case (1) the protective cocktail may be adjusted or changed, (2) the interference may be measured and accounted for, (3) the length of the incubation prior to addition of the DeathTRAK cocktail may be reduced, and/or (4) the loss of signal due to degradation and/or inactivation of G3PDH may be measured and taken into account. However, most of the small molecules and other agents of interest to high-throughput screening groups would not be significantly affected by exposure to such low levels of a reducing agent. Protease inhibitors would not be likely to have any effect on such compounds.

Figure 12:
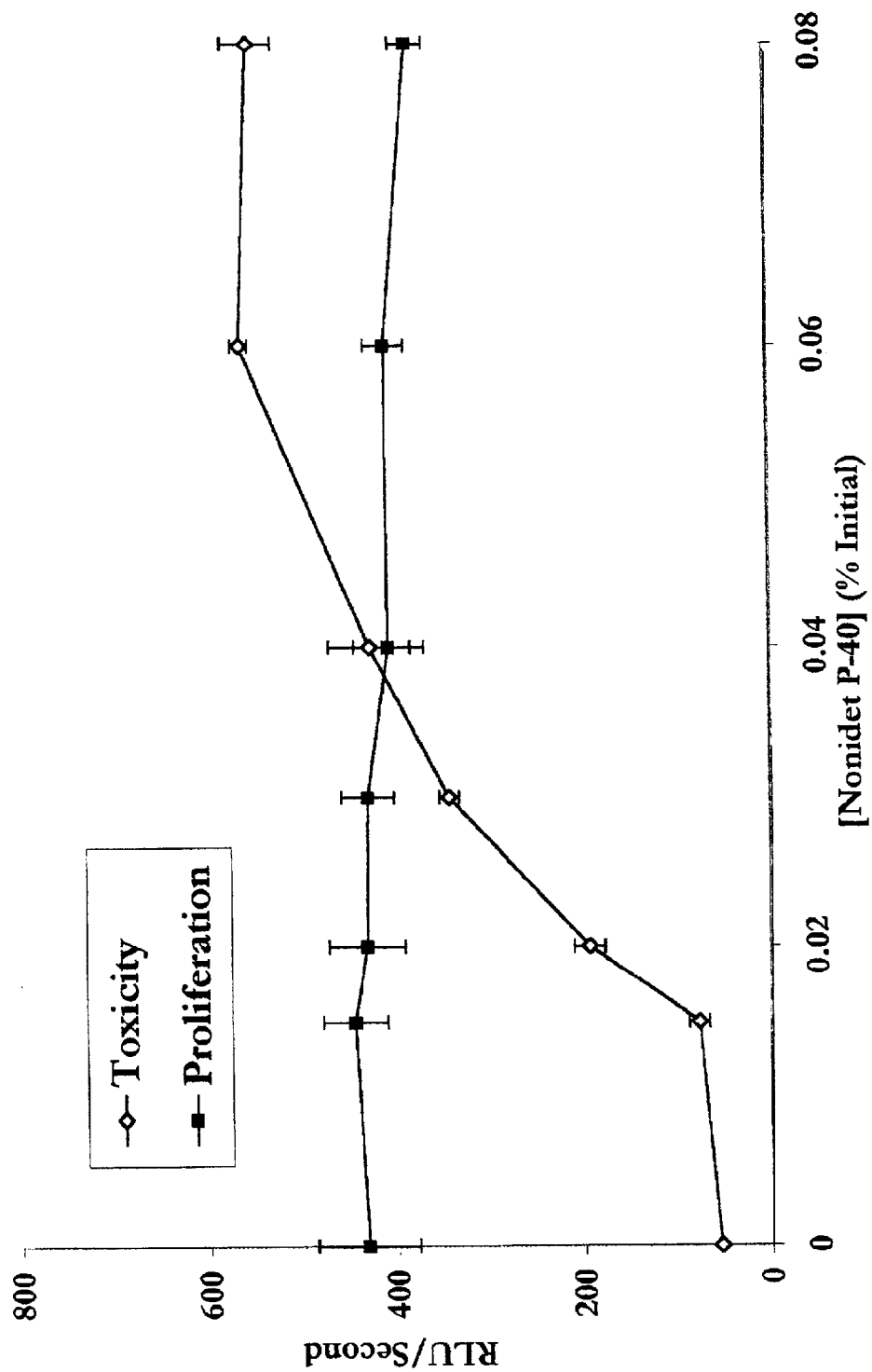
FIG. 12 shows the results of cytotoxicity/proliferation mode measurements made with the 841CON cell line, using the detergent Nonidet-P40 as both the toxin and the total-lytic agent.

FIG. 12 illustrates the use of cytotoxicity/proliferation mode to measure both the cytotoxic effects and the total cell number after addition of the detergent Nonidet P40 to the mammalian cell line 841 CON. Similar results have been obtained with the PC-3 prostate cancer and T24 bladder-cancer cell lines. In these experiments, the detergent is used as both the toxin and the final lytic agent. Thus the cytotoxicity signal in FIG. 12 represents the signal obtained after the indicated quantities of detergent were added to the cells, and the proliferation signal in the same figure represents the signals obtained after an additional 0.2% Nonidet P-40 was added to all the cells. Nonidet P-40 is a detergent that has an effect on the DeathTRAK signal—i.e., it reduces the signal by an amount which varies with the concentration up to approximately 45% inhibition at 0.1% Nonidet P-40, but changes very little above approximately 0.1%. Thus Nonidet P-40 can be used as the universal lytic agent for measuring proliferation of mammalian cells, provided that if it is desired to compare the cytotoxicity and proliferation signals, the final signal must be corrected for the inhibitory effect of the detergent. If the final detergent concentration used is above approximately 0.1%, then this correction will consist essentially of multiplication by a constant. However, if proliferation signals alone are to be compared, this correction is not necessary. Note that in FIG. 12, the proliferation signal is fairly constant. This is because each experiment began with the same number of cells seeded into each well. Thus the signal due to addition of the initial aliquot of detergent, as specified on the X-axis (cytotoxicity signal), added to the signal caused by the lytic aliquot of detergent (0.2%), yields a constant which is proportional to the cell number in the well at the beginning of the experiment.

Methods and compositions for the experiment illustrated in FIG. 12, and similar experiments with PC-3 and T24 cells, were as follows:

Cells were grown as for Example 1 and plated at a density of 1000 cells in 50 $\mu$L into individual wells of a 96-well white luminance microtiter plate, and then grown overnight. The volume in the morning was measured as approximately 40 $\mu$L per well. Since DeathTRAK is fully compatible with cell-culture media and growing cells, no washes were performed before initiation of the DeathTRAK assay. The toxins (which were simply the detergent Nonidet P-40 in this case, but could be drug candidate molecules or members of a chemical library) were added in 4.4 $\mu$L. (This detergent acts very quickly, and no further incubation was necessary; however, if an incubation were desired in order to give potential toxins time to act, then the user has the option of using the protective cocktail described in 8. This cocktail could be either added separately when the toxins are added, combined with the toxins in solution, or added to the original cell suspension; in the latter case, overnight growth would not be recommended, since the dithiothreitol would probably be oxidized during the overnight incubation.) Following addition of the toxin/detergent, 40 $\mu$L of the DeathTRAK cocktail was added. The cocktail composition was as follows:

TABLE III

Preferred Composition of DeathTRAK Cocktail
for Cytotoxicity Measurement

| Material | Volume (for 40-μL final volume) |
|---|---|
| Non-Labile Cocktail (explained below) | 37.75 μL |
| Reconstituted ATP Assay | 1.68 μL |
| H$_2$O | 0.44 μL |
| Phosphoglycerokinase stock (undiluted) | 0.008 μL |
| 100 mM ADP | 0.113 μL |

Since some of these quantities are difficult to measure, and for reproducibility purposes, the cocktail is generally made up for multiple wells in a single vessel; for example, in the current experiment, enough cocktail was made for 45 wells, as follows:

1.704 mL Non-Labile Cocktail
76 μL reconstituted ATP assay
20 μL H$_2$O
0.36 μL phosphoglycerokinase
5.1 μL 100 mM ADP Following addition of the DeathTRAK cocktail, luminance of the samples was read for 5 minutes (841 CON) or 2.5 minutes (PC-3). In general this step may be carried out for 0.1–10 minutes, depending primarily on the cycle speed of the luminometer being used. The lytic agent was then added: 0.9 μL of 10% Nonidet P-40 in H$_2$O. If automated injection is being used, this volume may be scaled up to an appropriate volume for automated injection (5 μL or more), using a correspondingly lower concentration of the detergent, without appreciable effect on the assay. Following addition of the lytic agent, the luminance was read again for the proliferation readout. The data were reduced by linear regression.

Composition of the Non-Labile Cocktail (NLC) was as follows:

TABLE IV

Composition of Non-Labile DeathTRAK Cocktail for
Cytotoxicity, Proliferation/Viability,
or Combined Mode Measurements

| Material | Volume |
|---|---|
| IMDM growth medium | 4.68 mL |
| PBS | 2.535 mL |
| 4XGP mixture, described above under Example 1 | 1.2675 mL |
| ATP Assay Diluent | 5.703 mL |
| 1M dithiothreitol | 0.006 mL |
| 100 mM ADP | 0.0045 mL |

Note that the ADP is an optional ingredient in the NLC. In some experiments, as in this Example, additional ADP is provided in the final cocktail. In general, the ADP may be provided in the NLC for convenience, or added as the final cocktail is made up so as to control the final concentration precisely and protect the ADP from any degradation caused by components of the NLC. The NLC may be stored for several months at −80C with little change in activity if the ADP is stored separately and added on the day of use, or approximately 1–3 weeks if the ADP is included.

Figure 13:
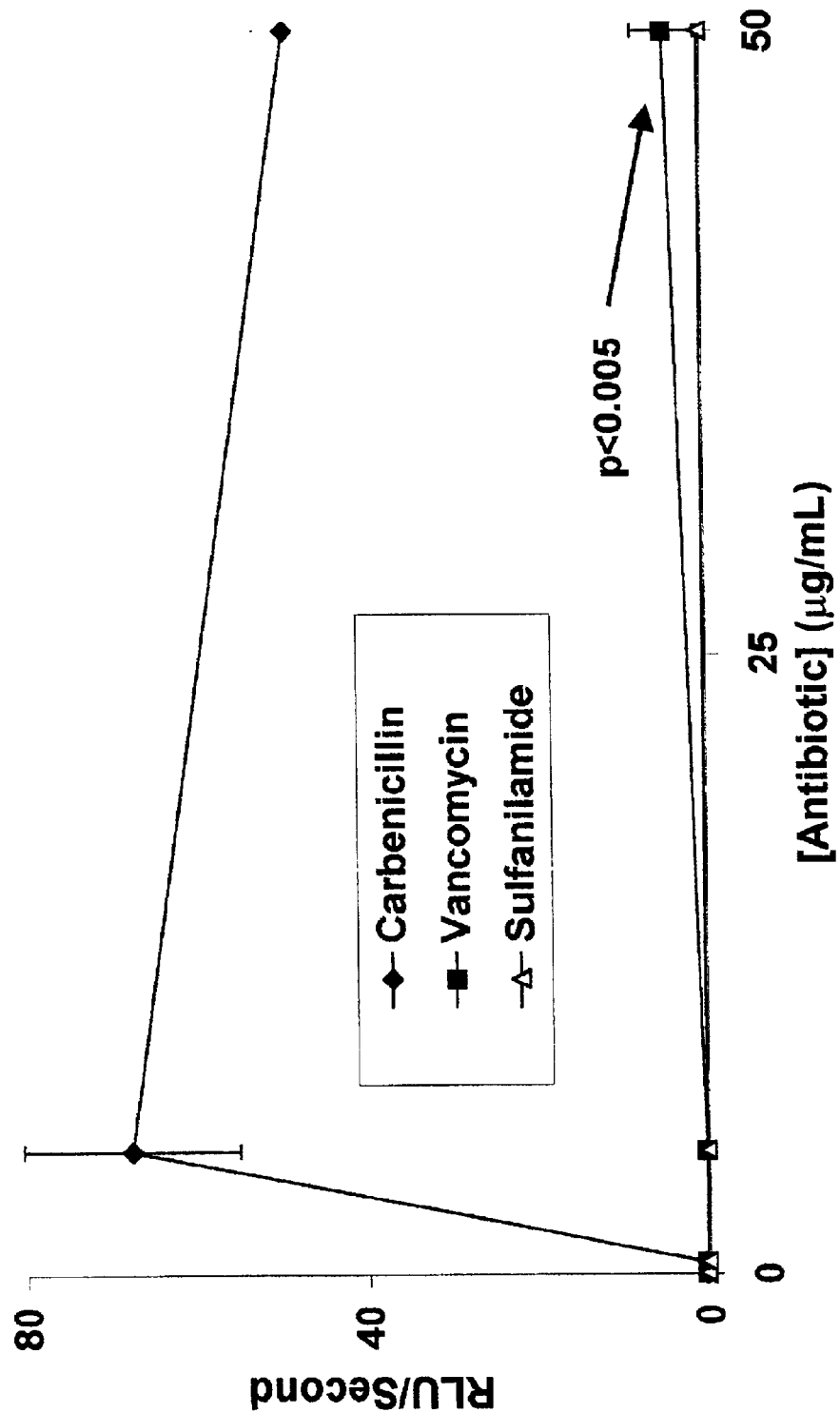
FIG. 13 shows the results of cytotoxicity mode measurements of the effects of three antibiotics, made with *E. coli* strain K1.
Figure 14:
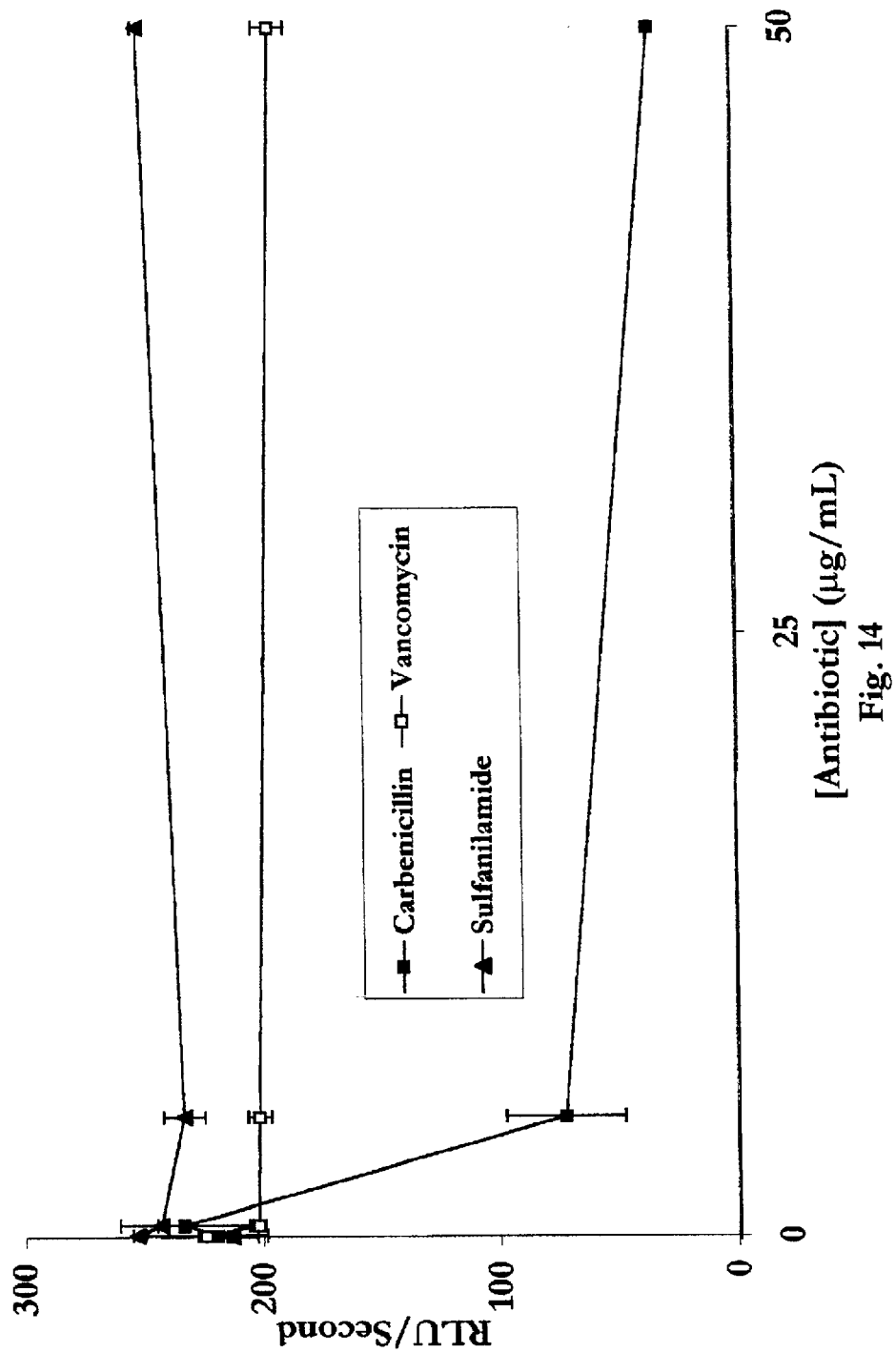
FIG. 14 shows the results of proliferation mode measurements made with *E. coli* strain K1, from the same experiment as the data of FIG. 13, following addition of the lytic agent, a polymyxin B/lysozyme combination.
Figure 15:
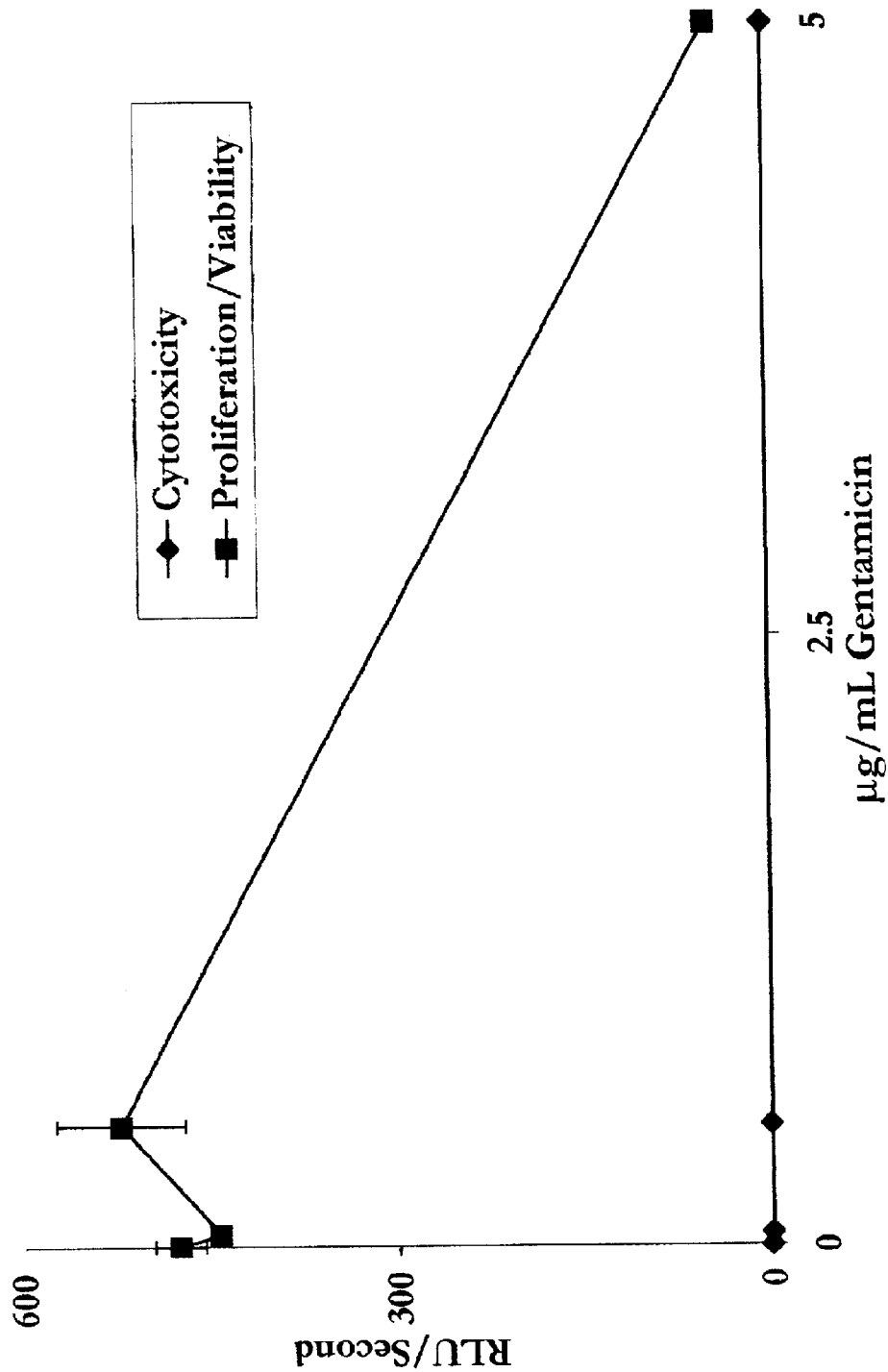
FIG. 15 shows both cytotoxicity and proliferation data from an experiment similar to those shown in FIGS. 13 and 14, using gentamicin with the *E. coli* K1 strain.

FIGS. 13–15 illustrate the use of cytotoxicity/proliferation mode to characterize the effects of various antibiotics on E. coli cells. First, the cytotoxicity signal was obtained by adding the DeathTRAK reagent cocktail directly to the toxicity reaction, three hours after the antibiotics were added to the E. coli culture. The luminance was measured and recorded (FIG. 13), whereupon the lytic agent was added, and the luminance was immediately measured again (FIG. 14). As is apparent from the figures, carbenicillin exhibited both strong cytotoxicity and a strong inhibitory effect on proliferation/viability. Vancomycin exhibited slight but statistically significant toxicity, and slight inhibition of proliferation/viability which is not significant by t-test but passes a rank-sum test. Sulfanilamide exhibited no toxicity or effect on proliferation/viability. Colony-forming unit (CFU) tests, in which the cultures were plated at various dilutions, confirmed that both carbenicillin and vancomycin were toxic, while sulfanilamide exhibited no toxicity by CFU assay at these concentrations. FIG. 15 shows the results of a similar experiment with gentamicin, which exhibited a strong effect on proliferation/viability, but no cytotoxicity in 90 minutes. In each case, the results of DeathTRAK are predictive of the known mechanisms of the respective antibiotics, as illustrated by the following table, where "+" indicates a cytotoxic or antiproliferative effect:

TABLE V

Antibiotic Effects on E. coli Measured and Mechanistic
Information Obtained Using DeathTRAK

| Antibiotic | Cytotoxicity | Proliferation/ Viability | Mechanism |
|---|---|---|---|
| Carbenicillin | + | + | Inhibits cell-wall synthesis |
| Vancomycin | + | + | Interferes with cell-wall cross-linking |
| Gentamicin | − | + | Inbibits protein synthesis, intracellular |
| Sulfanilamide | − | − | Not toxic at these concentrations |

Thus a clear advantage of the DeathTRAK method is that not only may effective anti-bacterial compounds be identified, but mechanistic information about the candidate antibiotics may also be collected at the same time, in an assay rapid enough for use in high-throughput screening.

Compositions for Bacterial DeathTRAK

Total Lysis of Gram Negatives

The Gram negative bacterium E. coli was killed in the total-lysis step with a mixture of polymyxin B and chicken lysozyme. Both components were necessary for the lysis to occur, and titration experiments established the optimal concentration of polymyxin B as ~300 units/mL and the optimal concentration of lysozyme as ~2.5% final. It will be evident to one skilled in the art that other pore-forming agents and other enzymes may be successfully substituted for polymyxin B and lysozyme, respectively, in this system.

Total-Lysis Experiments

E. coli were grown overnight in LB from refrigerated cultures, washed in LB, and resuspended to a final A$_{600}$ of 2.18. Lytic agents (polymyxin B, 30200 units/mL in PBS, lysozyme, 5% in PBS) were added (5 μL each to 45 μL of culture in luminance microtiter plate), whereupon 45 μL of DeathTRAK cocktail made up as for cytotoxicity/proliferation experiments was added and the luminance was read.

Preparation of E. coli

E. coli (strain K1, obtained from Dr. Craig Rubens of Children's Hospital and Regional Medical Center, Seattle, Wash.) were inoculated from a frozen permanent into 1–2 mL of LB, grown overnight, diluted 1:20 into LB, grown a further 106 minutes at 37C with 240 rpm shaking, harvested by centrifugation, washed twice with LB, and resuspended to a final A$_{600}$ of 1.549. It was determined by colony-forming unit assays that an A$_{600}$ of 2.18 corresponds to ~3.02×10⁸ cells/mL. This was diluted to 200,000/mL and a 10% volume of 10 mM dithiothreitol and 1% protease inhibitor cocktail in LB was added (yielding 0.1% protease inhibitor cocktail after mixing). 55 μL of this mixture was distributed to each test well of a 96-well white luminance microtiter plate, whereupon 5 μL of antibiotic or PBS (vehicle) was added. The plate was shaken at 240 rpm for 3 hours at 37C. 40 μL of DeathTRAK cocktail was then added and luminance was read for ~8 minutes. The lytic agent was then made up as equal parts 6000 units/mL polymyxin B and 50% lysozyme, both in PBS. 10 μL of this lytic agent was added to each well and the second luminance readout (proliferation/viability) was taken.

Figure 16:
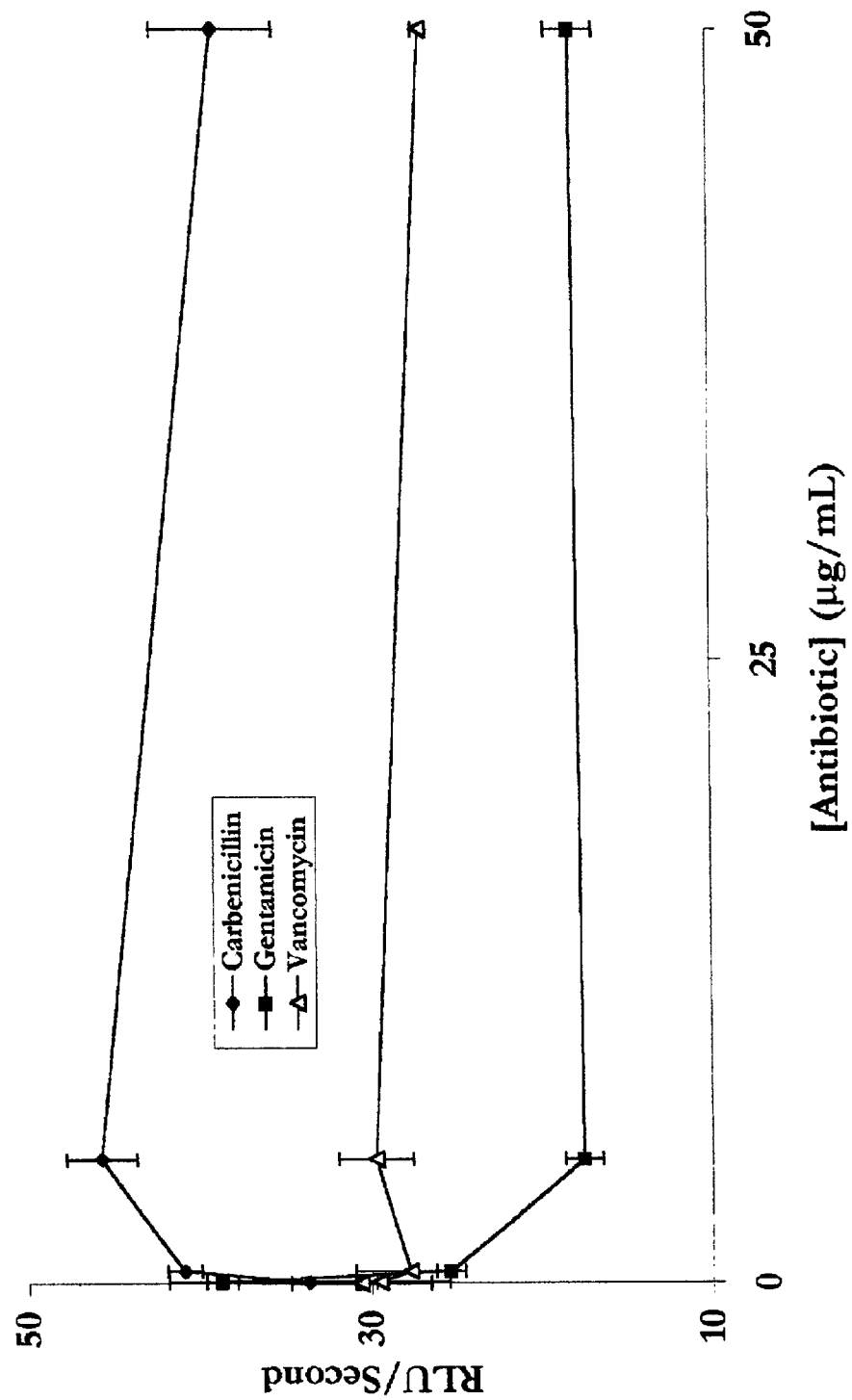
FIG. 16 shows the results of cytotoxicity mode measurements made with Group-A Streptococcus, using three antibiotics as toxins.
Figure 17:
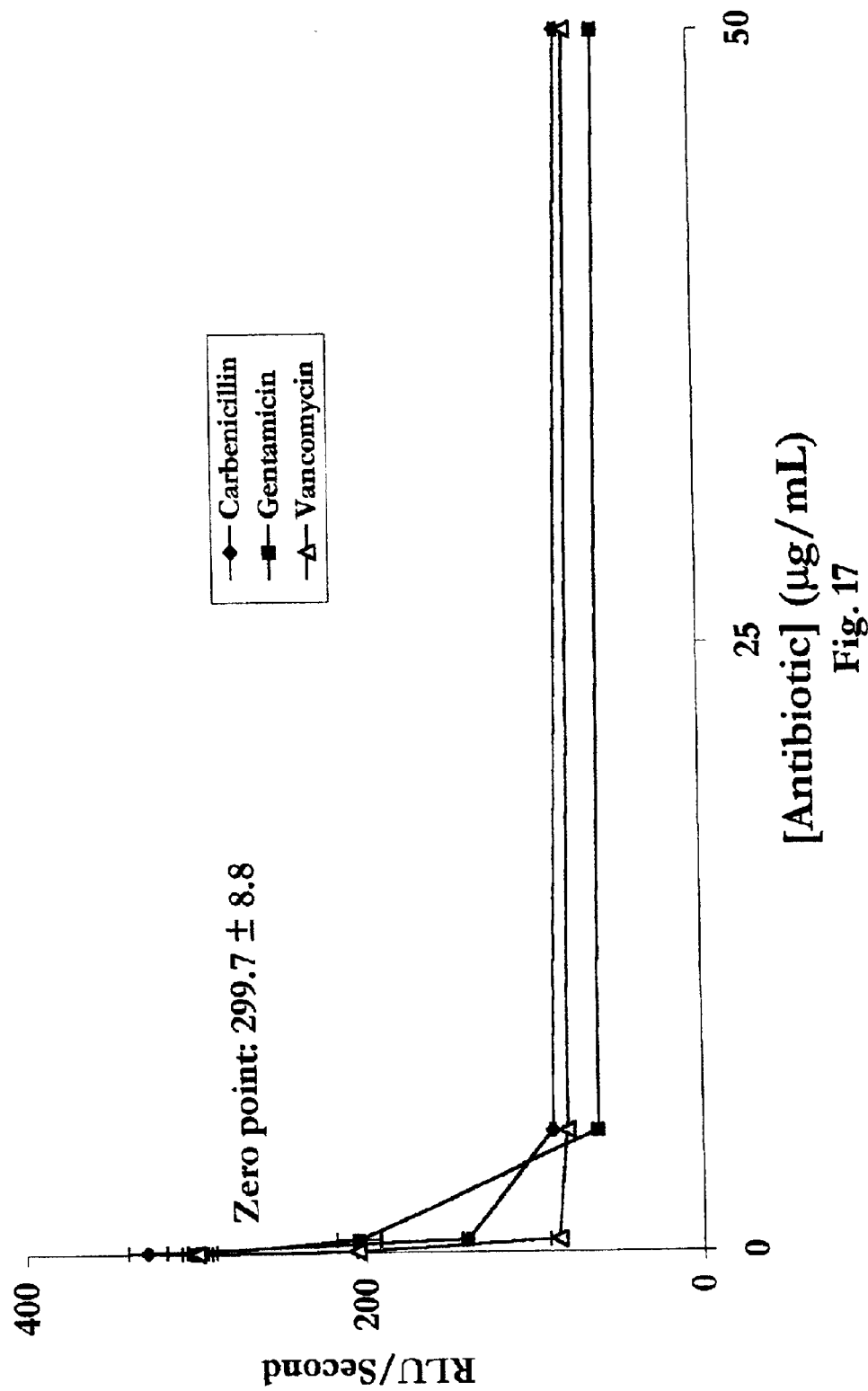
FIG. 17 shows the results of proliferation mode measurements made with Group-A Streptococcus, from the same experiment as the data of FIG. 16, following addition of the detergent Nonidet P40 as the total-lytic agent.

Results of Measurement of Cytotoxicity/Proliferation of Gram Positive Bacteria with DeathTRAK FIGS. 16 and 17 illustrate the use of cytotoxicity/proliferation mode to characterize the effects of various antibiotics on Group-A streptococci. These are Gram positive organisms. Since they lack an outer membrane and have much thicker cell walls, the effects of the antibiotics are, as expected, different from those observed with $E.\ coli$. However, both cytotoxicity and proliferation effects are seen. Thus carbenicillin is identified as a lytic agent, as it is with Gram negatives. Vancomycin exhibited little or no direct cytotoxicity, but yielded a very strong reduction in the proliferation/viability signal. This interesting result may indicate either that vancomycin has other effects on Gram positives, in addition to effects on cell wall cross-linking, or that with the very thick cell walls of Gram positives, the degree of inhibition required to kill the cell is lower than that needed to cause overt lysis. Finally, the result with gentamicin is distinctive. This compound yielded a negative toxicity signal, relative to the no-antibiotic signal. The explanation is that these Gram positives slowly leak G3PDH. Thus the cytotoxicity signals seen with the Group A streptococci represent the sum of G3PDH released by lysed cells and G3PDH leaking from live cells. In the case of gentamicin, which causes little lysis but strongly inhibits growth, there is no appreciable cytotoxicity, and there are also fewer cells present to leak enzyme; thus the apparent cytotoxicity signal is lower than that seen without antibiotic. However, these effects are clarified by the proliferation/viability data, which clearly show that gentamicin is strongly toxic. Thus in the dual mode, it is very unlikely that any useful non-lytic toxin would be missed due to the leakiness (because it would be identified in the viability wing), while the only compound known to cause rapid lysis of Group A streptococci (carbenicillin) was correctly identified in the cytotoxicity wing of this experiment. It should be noted that $E.\ coli$ do not exhibit this leakiness (see FIG. 10).

Methods and Compositions for DeathTRAK Cytotoxicity/Proliferation Mode (Gram Positive Bacteria)

Group-A Streptococci obtained from Dr. Craig Rubens of Children's Hospital and Regional Medical Center, Seattle, Wash. were inoculated from a frozen permanent and grown overnight in THY medium, then diluted 1:10 into THY and grown an additional 136 minutes, harvested, and washed twice into 50% of the growth volume. The $A_{600}$ was 0.356. They were diluted to 4,000,000/mL on the basis of the $A_{600}$/cell count relationship determined above for Gram negatives; however, these Gram positives are somewhat larger and therefore yield correspondingly fewer cells per $A_{600}$ unit. After washing the cells were grown for 90 minutes at 37C with 240 rpm shaking. Antibiotics or PBS (vehicle) were then added in 5 μL, and the protective cocktail containing dithiothreitol and protease inhibitor cocktail was added in a further 5 μL. The cells were incubated at 37C with 240 rpm shaking for a further 90 minutes, whereupon the DeathTRAK cocktail was added and the cytotoxicity read as described above for Gram negatives. The total-lysis agent, 10 μL of 2% Nonidet P-40, was then added, and the proliferation/viability signal was read as above for Gram negatives.

EXAMPLE 9

High-Throughput Screening for Cytotoxicity and/or Membrane Damage and/or Proliferation The DeathTRAK assay or another coupled luminescent assay as described below under Example 14 in high-throughput screening is a completely homogeneous assay, in that (1) only a single injection of the cocktail would be necessary, and (2) no manipulation by humans would be required after the assay cocktail was loaded for injection and the plate was placed in the luminometer. DeathTRAK can also be used with scintillation counters, spectrophotometers, and fluorometers. Again, the cocktail may be injected before, during, or after introduction of the potentially cytotoxic reagent. In the most rapid possible mode, the potentially cytotoxic reagent may be added simultaneously with the cocktail and the luminance readout could be taken within minutes, or possibly even in less than one minute. The proliferation mode as described in Example 7 may also be usefull in an HTS environment, especially since the sensitivity is greater than that of ATP-release assays. As described above, the readout of DeathTRAK and related assays may be analyzed by performing linear fits to determine the rate of increase of the luminance signal with time, or, more conveniently for high-throughput assays, by taking a single read at a constant, predetermined time after injection of the reagent cocktail and using this as the luminance readout.

EXAMPLE 10

Screening for Drug Resistance/Sensitivity

Samples of a patient's cells, or a culture of an infectious agent from a patient, may be screened against various drugs using DeathTRAK or another coupled luminescent assay as described below under Example 14 to determine sensitivity and/or resistance to the drugs. This may be accomplished in cytotoxicity, proliferation, or combined mode.

EXAMPLE 11

Measurement of Adoptosis

Determination of apoptosis may be carried out just as other forms of cytotoxicity are measured, using DeathTRAK or another coupled luminescent assay as described below under Example 14. Alternatively it may be possible to take advantage of the fact that apoptosis is associated with increased levels of G3PDH in the nucleus (Carlile et al., $Mol.\ Pharmacol.$ 57:2–12). This may be done, for example, by lysing equal numbers of cells and comparing levels of G3PDH activity via DeathTRAK. In another embodiment, apoptosis could be distinguished from necrosis by use of a simultaneous assay which is specific for apoptosis, such as the TUNEL assay. Since apoptosis is largely an internal cellular process, membrane rupture is a relatively late event in apoptosis compared with DNA fragmentation, caspase activation, and other associated events. TUNEL and caspase assays would therefore be expected to respond to apoptotic events on a different timescale from release assays, while necrosis would likely lead to a signal in a coupled-luminescent release assay, but not in an apoptotic assay. Comparison of the time-dependence of the signals from the two assays should therefore allow the user to separate apoptotic from necrotic cell death.

EXAMPLE 12

Monitoring for Sterility or Bioburden

Use of DeathTRAK or another coupled luminescent assay as described below under Example 14 for sterility or bioburden monitoring would be similar to use in proliferation mode. Liquid samples or swab samples may be tested by addition of a lytic reagent followed by the coupled luminescent assay. This method is much more sensitive than other liquid-phase methods in current use.

EXAMPLE 13

Monitoring for Sterility or Bioburden

In this mode, DeathTRAK or another coupled luminescent assay as described below under Example 14 typically would be used in combination with one or more standard cell lines or cell types Testing for shellfish toxins, for example, might involve the use of neuroblastoma cells in combination with reagents to distinguish sodium-channel blockers from enhancers, as previously described (Manger et al., *J AOAC Int*. 78:521–7, 1995). The MTT assay used in that work would be replaced by DeathTRAK or another coupled luminescent assay as described below under Example 14.

EXAMPLE 14

Extension to Other Coupled Luminescent Enzyme Systems

Coupled luminescent enzyme assays, as described herein, are extensible to other combinations of enzymes (Example 5: Aldolase-DeathTRAK). Other systems in which coupled luminescent assays of cytotoxicity are possible include:

(1) "Reverse" DeathTRAK in which G3PDH is supplied in the cocktail, but PGK is omitted and is the reagent under test.

(2) Measurement of release of pyruvate kinase. Like G3PDH, this enzyme makes ATP by phosphorylating ADP. The substrate of pyruvate kinase, phosphoenol pyruvate, is quite unstable but could be supplied, or generated in situ by the action of enolase on 2-phosphoglycerate.

(3) Measurement of release of lactate dehydrogenase. This enzyme interconverts pyruvate and lactate, simultaneously interconverting the reduced and oxidized forms of nicotinamide adenine dinucleotide. The reduced form, abbreviated NADH, is a substrate for certain bacterial luciferases. Some of these luciferases react very rapidly with NADH and may work better in a glow luminescence reaction than in a flash reaction. Both kinds of reactions are compatible with the coupled luminescent assay methods discussed herein. Either pyruvate or lactate may be supplied in the cocktail, and either disappearance or appearance of NADH would be measured by coupling with bacterial luciferase, respectively. This system may also be coupled to enzymes that generate pyruvate or lactate, or enzymes of the tricarboxylic acid cycle involved in NADH metabolism.

(4) Measurement of G3PDH release by measurement of NADH in a similar manner. Again, this system may be coupled to enzymes that generate G3P or 1,3 diphosphoglycerate (the product of G3PDH oxidative phosphorylation of G3P).

(5) Measurement of release of any kinase. Such kinases consume ATP, which would result in a detectable decrease in a luminance signal. However these enzymes can also be run "backwards" if the appropriate phosphorylated substrate is supplied, thus generating ATP.

(6) Measurement of release of isocitrate dehydrogenase by observing appearance/disappearance of NADH by flash luminescence.

(7) Measurement of release of succinyl-CoA synthase by coupling of ATP (or GTP) appearance or disappearance with luciferase luminescence.

(8) Measurement of phosphatases released by lysed cells, or phosphatases retained in the membranes of lysed cells, by the method described in Example 16. Note that the PhosTRAK components, like DeathTRAK, are compatible with the presence of live cells. In an alternative embodiment, the free phosphate released by lysed cells could be measured as in Examples 16 and 17 to quantify those cells.

(9) In general, measurement of release of any enzyme which produces and/or destroys ATP, NADH, or another molecule may be used as a luminescent substrate by luciferases.

EXAMPLE 15

Extension of Coupled Luminescent Assays to uses Other Than Measurement of Cytotoxicity, Membrane Damage, and Proliferation Cytotoxicity is not the only possible target of coupled luminescent assays. For example, specific kinases are of great interest in cancer research. Current specific kinase assays are mostly laborious, involving radioactively labelled substrates and physical separation of the phosphorylated target from the label, followed by scintillation counting. Instead, the DeathTRAK invention may be used to assay for specific kinase activity in at least one of two ways:

(1) ATP, ATP assay cocktail, and the target of the specific kinase are supplied in a master mix. If the specific kinase is present, the luminance signal will decrease with time as ATP is exhausted.

(2) If a positive signal is desired, the assay can be run in the reverse direction. This requires prior synthesis of the phosphorylated target, which will be problematic in some cases. The phosphorylated target, ADP, and ATP assay cocktail would be supplied. If the specific kinase is present, ATP will be created by the reverse action of the kinase and the luminance will increase with time.

Other uses of the DeathTRAK invention are:

(3) A coupled luminescent assay can be used for ultrasensitive detection of specific free amino acids. The corresponding aminoacyl-tRNA synthetases would be provided, possibly with a mixture of tRNAs (some of these enzymes do not require tRNA for the charging step). ATP? would be consumed by charging if the specific amino acid were present, causing a decrease in the luminance signal.

(4) Clinical laboratories often require ultrasensitive assays for enzymes such as lactate dehydrogenase and isocitrate dehydrogenase. These can be coupled to production or consumption of ATP by methods described above to give a luminescent readout. This method would probably be more sensitive than EIA methods.

(5) A number of types of ATPases have been characterized, including sodium/potassium-dependent, $F_0/F_1$, and proton-pump ATPases, all of which are of great biological importance in many organisms. In some cases, coupling of these ATP-destroying and/or creating activities to luminescent detection of ATP could represent an improved method of assaying these ATPases.

(6) One of the major battles in the struggle to defeat the trypanosome is the effort to find specific inhibitors of the glycolytic enzymes of these organisms, which differ significantly from the corresponding mammalian enzymes. Since DeathTRAK is really a G3PDH assay (and can be used as a PGK assay), it could be useful in high-throughput screening for differential inhibition of these enzymes (e.g., Bressi J C, Choe J, Hough M T, Buckner F S, Van Voorhis W C, Verlinde C L, Hol W G, Gelb M H, *J Med Chem* 2000 November 2;43(22):4135–50).

EXAMPLE 16

Measurement of Phoshatase Activity by PhosTRAK

Figure 18:
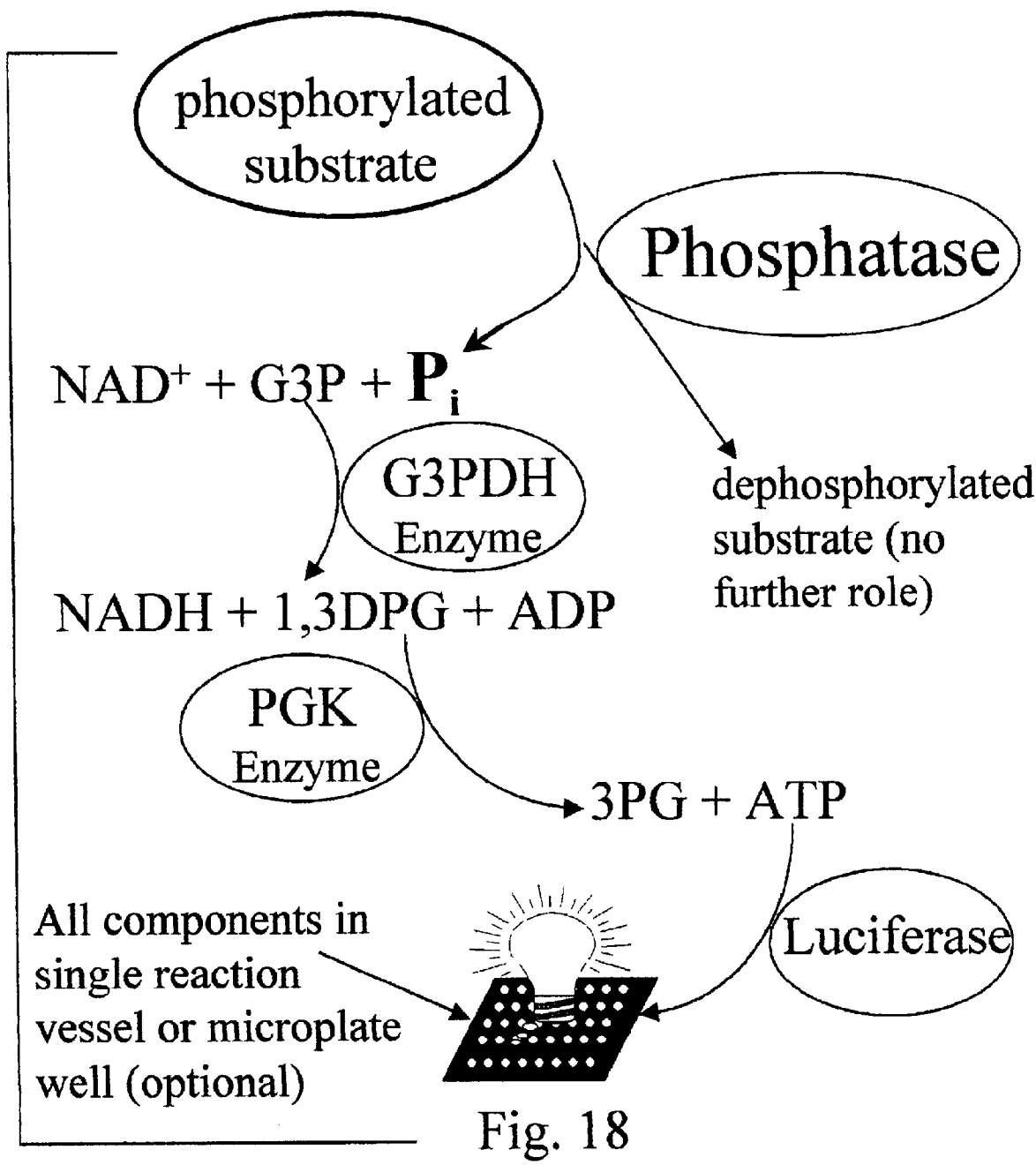
FIG. 18 is a schematic diagram of a preferred mode of the present invention known as "PhosTRAK," a rapid, homogeneous, luminescent phosphatase assay. Abbreviations used in FIG. 18: NAD+: nicotinamide adenine dinucleotide (oxidized form); G3P: glyceraldehyde-3-phosphate; $P_i$: phosphate ion; G3PDH: glyceraldehyde-3-phosphate dehydrogenase; NADH: nicotinamide adenine dinucleotide (reduced form); 1,3DPG: 1,3 diphosphoglycerate; ADP: adenosine diphosphate; PGK: phosphoglycerokinase; 3PG: 3-phosphoglycerate; ATP: adenosine triphosphate.

PhosTRAK is an assay for free phosphate, and therefore for the activity of phosphatases, enzymes which liberate free phosphate. The reaction scheme of PhosTRAK is nearly identical with that of DeathTRAK as can be seen from FIG. 18, which is similar to FIG. 1, the schematic representation of DeathTRAK. The critical difference is that in PhosTRAK, the reagent being measured is free phosphate, which must therefore be the limiting reagent. This implies that G3PDH, which is the limiting reagent in DeathTRAK, must be present in PhosTRAK, and it is therefore supplied in the cocktail. Conversely, the reagents used for PhosTRAK (other than the test sample) should be made as free of phosphate as is practicable, in order to reduce the background signal from endogenous phosphate in the cocktail; however, even if substantial phosphate contamination is present, it is still possible to perform PhosTRAK by subtracting the constant background signal due to endogenous phosphate or phosphate contaminating the phosphatase preparation (or other substances added by the user) from the time-dependent increase in luminance due to release of phosphate by the phosphatase.

The buffer used for phosphatase assays may be identical or similar to that used for the DeathTRAK cytotoxicity assay, with the following exceptions:

(A) Buffers, enzymes, and other components should be rendered as free of inorganic phosphate ion as is practicable. Instead of the sodium phosphate buffer used for DeathTRAK, the PhosTRAK buffer is a Tris-based buffer, described below as "reduced-phosphate cocktail."

(B) G3PDH is supplied in the PhosTRAK cocktail.

(C) Buffer components, small molecules, cofactors, and other elements essential to measurement of the activity of the phosphatase under study, made as free of phosphate as is practicable, are added to the reaction mixture.

A phosphatase assay performed in this manner may be used for the purposes of identifying inhibitors, enhancers, or other modulators of phosphatase activity (for example, molecules which change the pH profile or substrate-response profile of a phosphatase, or alter the manner in which the phosphatase responds to another regulatory molecule). Such a phosphatase assay may be used in conjunction with high-throughput screening methods, such as robotics, with or without automated injection and transfers, for example, to screen or test chemical libraries for inhibiting, enhancing, or modulatory activities against phosphatases.

Figure 19:
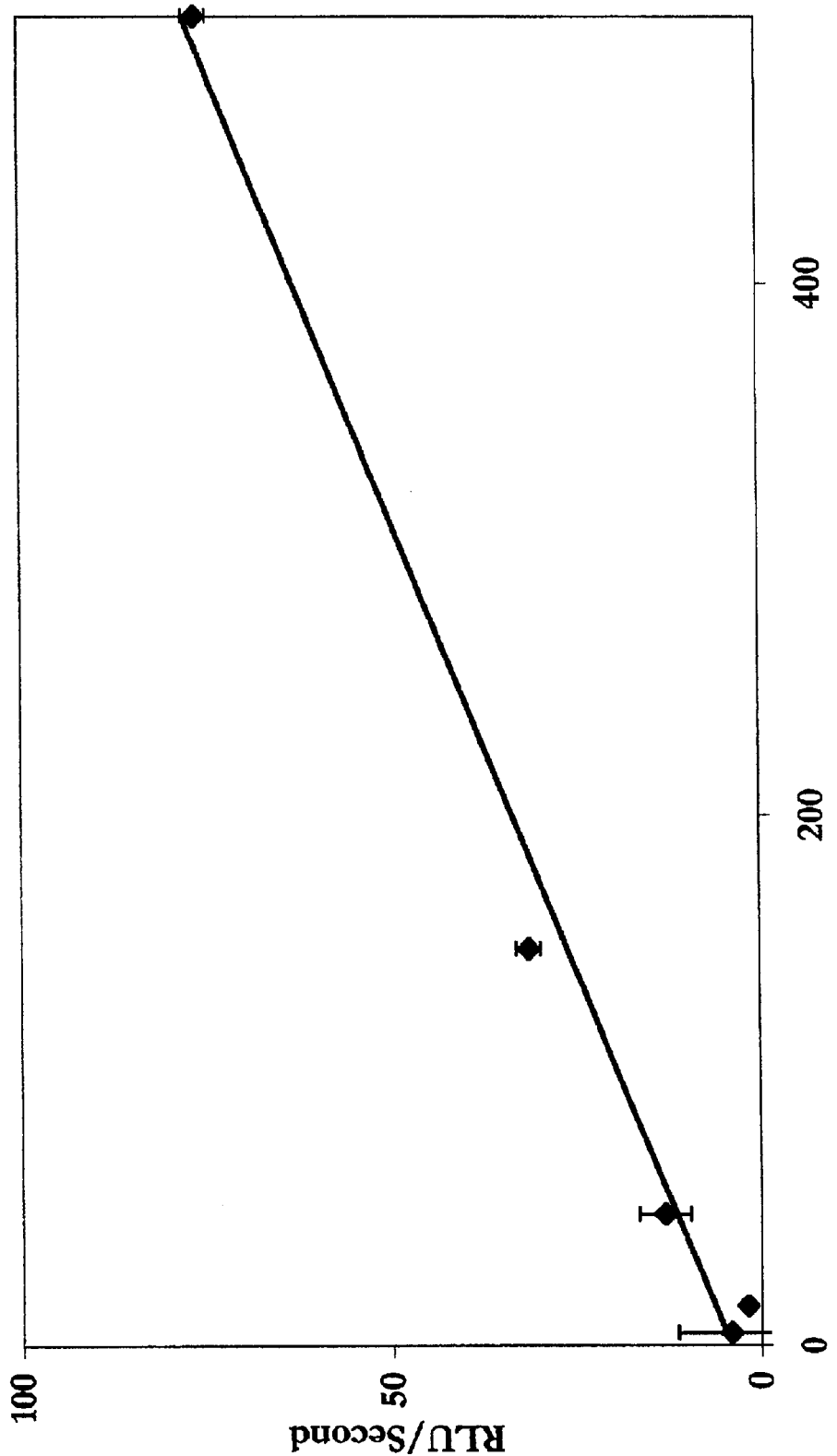
FIG. 19 demonstrates quantification of free phosphate using the PhosTRAK assay.

FIG. 19 shows the results of an experiment in which free phosphate was detected using PhosTRAK. A reduced-phosphate cocktail was made up as follows:

75 $\mu$L 1M Tris-HCL pH 7.4

647 $\mu$L H$_2$O 1.25 $\mu$L PGK diluted 1:10,000 with PGK diluent

570 $\mu$L ATP Assay diluent

63 $\mu$L ATP Assay 0.6 $\mu$L 1M dithiothreitol 0.75 L G3PDH, Sigma catalog #G-9263, diluted 1:100 with G3PDH diluent 121 $\mu$L of special 4XGP cocktail made up without free phosphate G3PDH diluent was made up as follows:

1000 parts phosphate-free PGK diluent 1 part 1M dithiothreitol

Composition of Special 4XGP cocktail without free phosphate was as follows:

2 mL 5× phosphate-free PGK diluent

10 $\mu$L 1M dithiothreitol

100 $\mu$L 100 mM NAD+

286 $\mu$L H$_2$O

Composition of 5× phosphate-free PGK diluent

666 $\mu$L triethanolamine 2.5 mL 1M Tris pH 7.4

259 $\mu$L 193 mM EDTA pH 8.0

5 mg five-times recrystallized BSA

Titrated to pH 7.3 with HCL, made up to 10 mL with H$_2$O The reduced-phosphate cocktail was supplemented with 0.9 $\mu$L of 10 mM ADP and was made 3 $\mu$M in glyceraldehyde-3-phosphate (Sigma catalog # G5251). 45 $\mu$L of the reduced cocktail was distributed into each test well of a luminescent microtiter plate. 5 $\mu$L of phosphate solution or H$_2$O was added to yield the total amounts of free phosphate indicated in the X-axis of FIG. 19, and the luminance was read for six minutes. The reactions were done in triplicate. Data from the first 160 seconds of the run were taken for analysis. The background level due to free phosphate present in the cocktail was subtracted from the data. Measurements of the signal-to-background ratio at various concentrations of glyceraldehyde-3-phosphate showed that this background is largely due to free phosphate present in the glyceraldehyde-3-phosphate preparation. The use of purified glyceraldehyde-3-phosphate would therefore ameliorate this background problem. (As an alternative, making glyceraldehyde-3-phosphate from glyceraldehyde-3-phosphate diethyl acetal barium salt, a new product from Sigma (catalog #G-5376), should produce glyceraldehyde-3-phosphate with a lower concentration of contaminating free phosphate.) In these experiments the signal-to-background ratio increased with decreasing glyceraldehyde-3-phosphate down to 3 $\mu$M. The size of the background signal indicated that 300–500 nM free phosphate was added with 3 $\mu$M glyceraldehyde-3-phosphate, for a contamination level of 10–15%. It should be possible to reduce this by at least five- to ten-fold by purifying the glyceraldehyde-3-phosphate prior to use in the assay.

Figure 20:
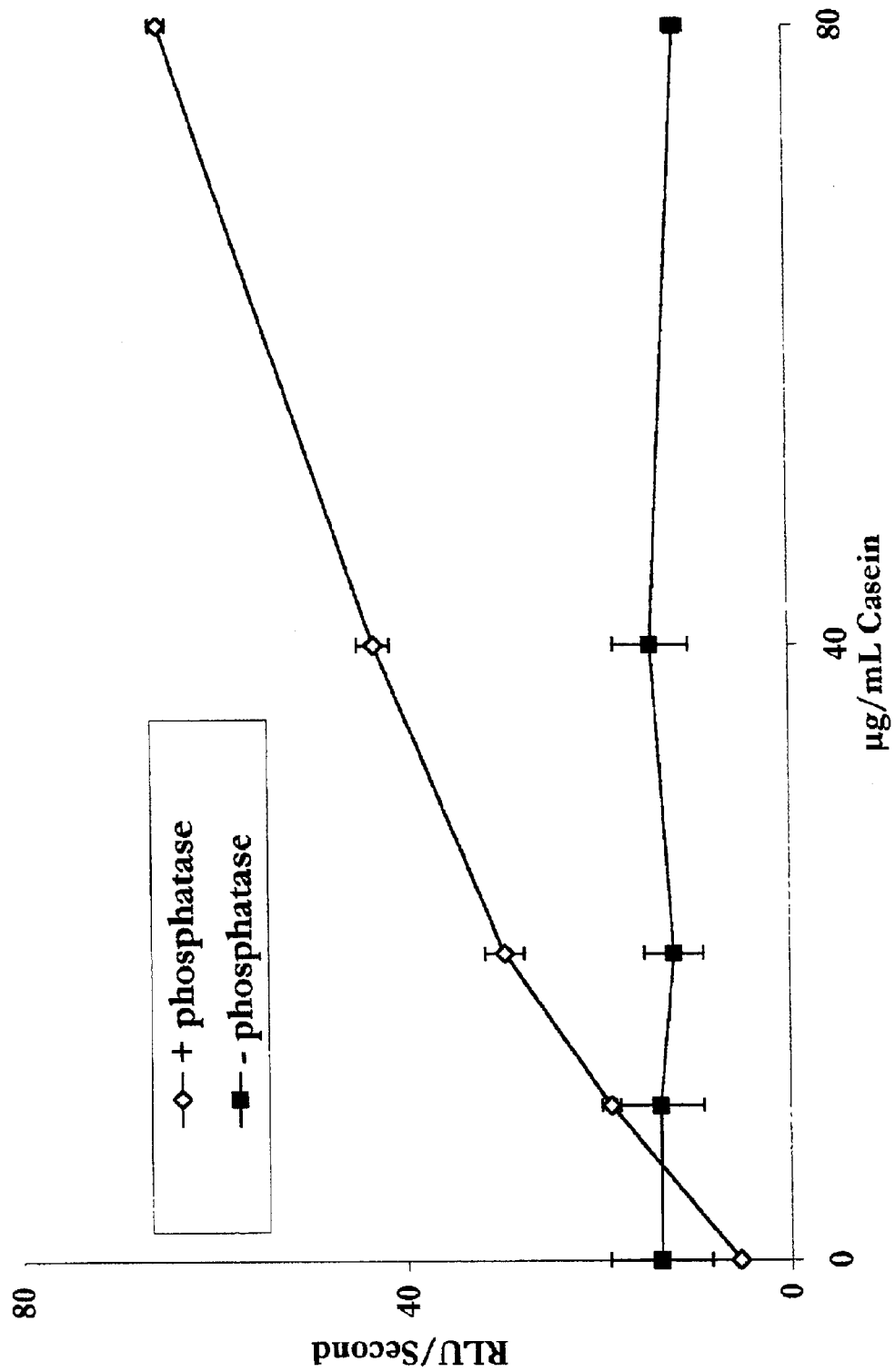
FIG. 20 shows the results of an experiment in which the activity of λ-phosphatase against casein was detected using the PhosTRAK assay.

FIG. 20 shows the results of an experiment in which the activity of $\lambda$-phosphatase was detected with PhosTRAK. For this experiment the following cocktail was made:

75 $\mu$L 1M Tris-HCL pH 7.4

1.25 $\mu$L PGK diluted 1:10,000 with PGK diluent

121 $\mu$L special 4×GP phosphate-free cocktail

570 $\mu$L ATP Assay diluent

63 $\mu$L ATP Assay

3 $\mu$L 1M dithiothreitol 0.75 $\mu$L G3PDH diluted 1:100 with G3PDH diluent 0.9 $\mu$L 10 mM ADP 1.5 µL 2.88 mM glyceraldehyde-3-phosphate
6 µL 500 MM MnCl₂
507.6 µL H₂O To 600 µL of this cocktail was added 1 µL λ-phosphatase (Sigma catalog #P-9614). Another 600-µL aliquot did not receive phosphatase. 45 µL of each of these respective aliquots was transferred in duplicate to wells of a luminance microtiter plate, and the indicated final concentrations of purified α-casein were achieved by addition of 5 µL of appropriate dilutions of casein in H₂O.

The activity of the phosphatase calcineurin was also detected with PhosTRAK. A phosphatase non-labile cocktail was made up as follows:

225 µL 1M Tris-HCl pH 7.4
363 µL special 4XGP, as used for assaying λ-phosphatase
1.71 mL ATP Assay diluent
9 µL 1M dithiothreitol
2.7 µL 100 mM ADP
4.5 µL 2.8 mM glyceraldehyde-3-phosphate
1.543 mL H₂O The final reaction cocktail was made up as follows:

1.285 mL above-described non-labile cocktail
63 µL ATP Assay
1.25 µL PGK diluted 1:10,000 with PGK diluent
0.75 µL G3PDH diluted 1:100 with G3PDH diluent Calmodulin was made up to 250 nM in a reaction buffer supplied with a kit from Calbiochem (catalog #207005). 50 µL of this mixture was distributed to wells of a luminance microtiter plate. A 1% volume of calcineurin (8 units/µL) from the same kit was then added to the calmodulin solution and 50 µL of this mixture were transferred to positive wells. Negative wells did not contain calcineurin. Purified a-casein in PGK diluent was added to 40 µg/mL (final concentration) in 5 µL, whereupon the reactions were incubated for 30 minutes at room temperature. After the incubation, the final reaction cocktail was added (45 µL) to each well and the luminance was read.

The results of the assay were: +calcineurin, 2.99±0.47 RLU/Sec; –calcineurin, 2.30±0.06 RLU/Sec. The results of the assay show that a signal due to calcineurin is detected, but the background signal due to endogenous free phosphate is high. The use of purified glyceraldehyde-3-phosphate would improve the signal-to-background ratio in the detection of calcineurin activity.

EXAMPLE 17

Other Applications of Phosphate and Phosphate and Phosphatase Detection by PhosTRAK Detection of free phosphate by the methods described under Example 16 would be useful in a number of areas. Apart from measurement of phosphatase activity, detection of free phosphate could have applications in measurement or detection of other enzymatic, chemical, or biochemical reactions, including (A) pyrophosphatase activity, (B) spontaneous or catalyzed breakdown of nucleotide triphosphates, phosphorylated proteins, or other phosphate esters or diesters. PhosTRAK can be coupled to other systems in which free phosphate is a substrate, intermediate, or product to help in monitoring such reactions, or could be coupled to the action of a pyrophosphatase to allow quantification of any activity involving release of pyrophosphate. However, care must be taken in quantification of pyrophosphate, since the PhosTRAK system itself involves production of pyrophosphate, which could represent a background signal for which a correction would be made. Detection of free phosphate could also be useful in environmental monitoring. Eutrophication of bodies of water is often accompanied by a rise in the phosphate concentration. The presence of phosphate is frequently representative of the release into ground water of certain detergents and/or other compounds.

In a further embodiment of the present invention, the coupled luminescent detection system of PhosTRAK could be used to detect the activity of a phosphatase coupled or conjugated to other proteins or other molecules in ELISA, PCR, RT-PCR, Westerns, immunohistochemitry, in situ hybridization, or other techniques involving detection of a target or event by enzymatic labeling.

In a further embodiment of the present invention, the coupled luminescent detection of PhosTRAK could be used to detect the presence of inhibitors of phosphatases in the environment, in food samples, in research situations, or in other cases in which phosphatase inhibitors are of importance. Such an approach might be used, for example, to detect the toxin okadaic acid in shellfish extracts.

All publications and patent applications mentioned in this specification are herein incorporated by reference to the same extent as if each individual publication or patent application was specifically and individually incorporated by reference.

From the foregoing, it will be appreciated that, although, specific embodiments of the invention have been described herein for purposes of illustration, various modifications may be made without deviating from the spirit and scope of the invention.

We claim:

1. A method of measuring cell death or membrane damage in a mixture of dead and living cells or in a supernate therefrom, comprising determining in a sample of a mixture of dead and living cells or a supernate from the mixture the concentration of a high-energy molecule, by a luminescent reaction employing a luciferase, wherein an enzyme or enzymes is naturally present in the living cells being studied, and, when released from the dead cells, increases or decreases the concentration of the high-energy molecule by a reaction or reactions, whereby all the reactions necessary to produce the light output are initiated when the sample is contacted with a single reagent mixture.

2. The method of claim 1, wherein the enzyme or enzymes released is/are present in all known living cells.

3. The method of claim 2, wherein activity of the enzyme or enzymes released from the dead cells is coupled to that of one or more additional enzymes, such that a reaction product or products of said released enzyme or enzymes is a reaction substrate or substrates of one or more of said additional enzyme or enzymes, whereby said additional enzyme or enzymes increase or decrease the concentration of the high-energy molecule.

4. The method of claim 3, wherein the luciferase is firefly luciferase, the enzyme released from the dead cells is glyceraldehyde-3-phosphate dehydrogenase, and the activity of the enzyme released is coupled to that of the additional enzyme phosphoglycerokinase to produce the high-energy molecule ATP.

5. The method of claim 4, wherein the sample is treated to convert living cells to dead cells prior to, simultaneously with, or after contact with the single reagent mixture, and the luminance signal generated thereby is read at any point or points in the process subsequent to addition of the reagent mixture, which may be before, after, or both before and after the conversion of live cells to dead cells.

6. The method of claim 4, wherein a potentially cytotoxic agent is added to the sample, prior to or simultaneous with contact with the single reagent mixture.

7. The method of claim 5, wherein the cells to be measured for cytotoxicity, killed, and measured again for total biomass, are nucleated eukaryotic cells.

8. The method of claim 5, wherein the cells are killed by addition of a detergent which has either negligible or predictable and reproducible effects on the performance of the cytotoxicity assay.

9. The method of claim 8, wherein the detergent is Nonidet P-40, NP-40, or Brij.

10. The method of claim 5, wherein the cells to be measured for cytotoxicity, killed, and measured again for total biomass, are Gram-negative bacteria.

11. The method of claim 10, wherein the cells are killed by a mixture of a pore-forming agent and an enzyme which digests the cell wall.

12. The method of claim 11 wherein the pore-forming agent is Polymyxin B and the digestive enzyme is lysozyme.

13. The method of claim 5 wherein the cells to be measured for cytotoxicity, killed, and measured again for total biomass, are Gram-positive bacteria.

14. A method of measuring or monitoring the concentration of free inorganic phosphate in a sample, comprising contacting the sample with glyceralde-3-phosphate dehydrogenase, phosphoglycerokinase, and luciferase in a coupled reaction system, together with appropriate buffer constituents, cofactors, and substrates for the respective enzymes, such that luminance emitted by the system is related to the concentration of free phosphate.

15. The method of claim 14 wherein the buffers and other constituents used, apart from the phosphate source being tested, are wholly or substantially free of phosphate.

16. The method of claim 14 wherein the free phosphate concentration thereby measured or monitored indicates the activity of a phosphatase.

17. The method of claim 16, wherein the phosphatase is a protein phosphatase.

18. The method of claim 17, wherein the phosphatase is a protein tyrosine phosphatase.

19. The method of claim 16, wherein the activity of the phosphatase thereby measured or monitored identifies inhibitors or other modulators of the activity of the phosphatase.

20. The method of claim 16, wherein the phosphatase activity takes place under conditions that are incompatible with the light reaction described, but wherein the phosphatase is contacted by one or more substrates in a first step, whereupon in a second step the conditions are adjusted appropriately for operation of the light reaction described and the light reaction is used to detect free phosphate.

21. The method of claim 1, wherein the high-energy molecule is at least one of NADH, NADPH, and ATP.

* * * * *